ID

US007303895B1

(12) United States Patent
O'Regan et al.

(10) Patent No.: US 7,303,895 B1
(45) Date of Patent: Dec. 4, 2007

(54) CHOLINE TRANSPORT LIKE (CTL) MEMBRANE PROTEINS INVOLVED IN CHOLINE TRANSPORT

(75) Inventors: Seana O'Regan, Les Loges en Josas (FR); François Meunier, Gif sur Yvette (FR); Elisabeth Traiffort, Paris (FR); Martial Ruat, Bourg la Reine (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 546 days.

(21) Appl. No.: 10/129,440

(22) PCT Filed: Nov. 3, 2000

(86) PCT No.: PCT/FR00/03069

§ 371 (c)(1),
(2), (4) Date: Feb. 3, 2003

(87) PCT Pub. No.: WO01/32704

PCT Pub. Date: May 10, 2001

(30) Foreign Application Priority Data

Nov. 5, 1999 (FR) .................................. 99 13883

(51) Int. Cl.
*C12P 21/06* (2006.01)
*C12N 15/00* (2006.01)
*C12N 15/09* (2006.01)
*G01N 33/567* (2006.01)
*C07H 21/02* (2006.01)
*C07H 21/04* (2006.01)
*C12Q 1/68* (2006.01)

(52) U.S. Cl. ...................... 435/69.1; 435/320.1; 435/6; 536/23.1; 536/24.3; 436/504

(58) Field of Classification Search ............... 435/69.1, 435/320.1, 7.1, 6; 536/23.1, 23.5; 530/350
See application file for complete search history.

(56) References Cited

U.S. PATENT DOCUMENTS

2003/0109690 A1* 6/2003 Ruben et al. ............... 536/23.1

FOREIGN PATENT DOCUMENTS

| WO | WO 98/07859 | 2/1998 |
| WO | WO 98 07859 A | 2/1998 |
| WO | WO 98/27205 | 6/1998 |
| WO | WO 98 27205 A | 6/1998 |
| WO | WO 98/45435 | 10/1998 |
| WO | WO 98 45435 A | 10/1998 |
| WO | WO 98/45436 | 10/1998 |
| WO | WO 98 45436 A | 10/1998 |
| WO | WO 99/06439 | 2/1999 |
| WO | WO 99 06439 A | 2/1999 |
| WO | WO 98 26973 A | 6/1999 |
| WO | WO 99/26973 | 6/1999 |

OTHER PUBLICATIONS

Skolnick et al., 2000, TIBTECH, vol. 18, pp. 34-39.*
Bork et al., 1998, Current Opinion in Structural Biology, 8, pp. 331-332. et al.*
Nathwani et al., 2004, Vox Sanguinis, 87, pp. 73-81.*
Nyberg et al., 2004, Mol. Therapy, vol. 10, No. 6, pp. 976-980.*
Nikawa et al., "Cloning of a Gene Encoding Choline Transport in Saccharomyces-Cerevisiae," Journal of Bacteriology, vol. 166, No. 1, 1986, pp. 328-330, XP-000925069.
Database EMBL Nucleotide and Protein Sequences, Feb. 18, 1996, XP-002142601, Hinxton, GB, Soares Multiple Sclerosis 2NbHMSP *Homo sapiens* cDNA Clone MAGE:280448 3' Similar to gb:M74090, Polyposis Locus Protein 1 (HUMAN).
Database EMBL Nucleotide and Protein Sequences, Nov. 1, 1999, XP-002142602, Hinxton, GB, Rowen et al., "Sequence of the Human Major Histocompatibility Complex Class III Region," submitted Mar. 1999 to the EMBL/GenBank/DDBJ databases.
J. Nikawa et al., "Cloning of a Gene Encoding Choline Transport in Saccharomyces-Cerevisiae," *Journal of Bacteriology*, 1986, 166(1):328-330, XP000925069.
W. Mayser et al., "Primary Structure and Functional Expression of a Choline Transporter Expressed in the Rat Nervous System," *FEBS letters*, 1992 305(1):31-36, XP000915418.
H. Varoqui et al., "Cloning and expression of the vesamicol binding protein from the marine ray Torpedo: Homology with the putative vsicular acetylcholine transporter (UNC-17) from *Caenorthabditis elegants*," *FEBS letters*, 1994, 342(1):97-102, XP000915417.
Database EMBL Nucleotide and Protein Sequences, Jun. 30, 1999, XP002142598 Hinxton, GB, *Homo sapiens* cDNA clone IMAGE:2381639 3'. (Abstract).
Database EMBL Nucleotide and Protein Sequences, Aug. 18, 1998, XP00214599, Hinxton, GB, *Homo sapiens* cDAN clone IMAGE:1750845 3' (Abstract).
Database EMBL Nucleotide and Protein Sequences, Feb. 6, 1998, XP002142600, Hinxton, GB, *Stratagens schizo* brain S11 *Homo sapiens* cDAN clone IMAGE:971135 3' (Abstract).
Database EMBL Nucleotide and Protein Sequences, Feb. 6, 1998, XP002142601, Hinxton, GB, *Homo sapiens* cDAN clone IMAGE:280448 3' (Abstract).

(Continued)

*Primary Examiner*—Olga N. Chernyshev
(74) *Attorney, Agent, or Firm*—Foley & Lardner LLP

(57) ABSTRACT

The invention concerns the identification of a novel family of CTL (Choline Transporter Like) genes, in particular hCTL1 and hCTL2, involved in the metabolism and/or transport of choline in cells such as the intestinal tract cells, nervous cells, in particular motoneurons, sensitive neurons, neurons of the nucleus dorsalis of the spinal cord and oligodendrocytes. The invention opens up new prospects in particular for the treatment of familial dysautonomia, and Tangier disease. More generally, the identification of CTL genes enables to develop new strategies for treating diseases of the nervous system, in particular neurodegenerative demyelenating diseases, particularly Alzheimer disease, Parkinson disease and Huntington disease.

8 Claims, 17 Drawing Sheets

OTHER PUBLICATIONS

Figure 1A:
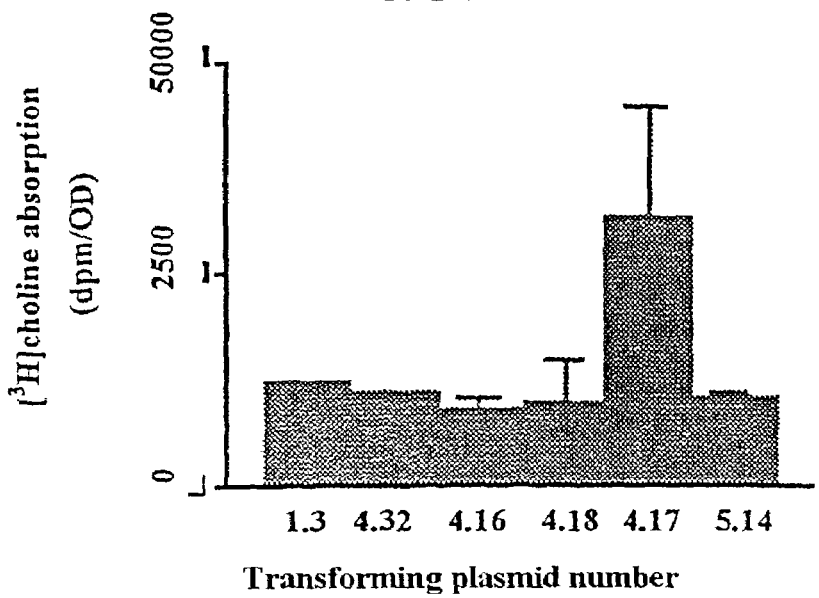

Database EMBL Nucleotide and Protein Sequences, Nov. 1, 1999, XP002142602, Hinxton, GB, Rowen L. et al., Sequence of the human major histocompatibility complex class III region., (Abstract).

S. O'Regan et al., "An electric lobe suppressor for a yeast choline transport mutation belongs to a new family of transporter-like proteins," *Prod. Of Nat. Acad of Sciences*, Feb. 2000, 97(4):1835-1840.

* cited by examiner

```
          10        20        30        40        50        60        70        80
          ....|....|....|....|....|....|....|....|....|....|....|....|....|....|....|....|
hCTL1_a-  HGCCSSASSAAQSSKREWKPLEDRSCTDIPWLLLFILFCIGHGFICGFSIATGAAARLVSGYDSYGNIRGQKNTKLEAIP 80
hCTL1_b-  MGCCSSASSAAQSSKREWKPLEDRSCTDIPWLLLFILFCIGHGFICGFSIATGAAARLVSGYDSYGNIRGQKNTKLEAIP 80

90        100       110       120       130       140       150       160
          ....|....|....|....|....|....|....|....|....|....|....|....|....|....|....|....|
hCTL1_a-  NSGMDHTQRKYVFFLDPCNLDLINRKIKSVALCVAACPRQELKTLSDVQKFAEINGSALCSYNLKPSEYTTSPKSSVLCP 160
hCTL1_b-  NSGMDHTQRKYVFFLDPCNLDLINRKIKSVALCVAACPRQELKTLSDVQKFAEINGSALCSYNLKPSEYTTSPKSSVLCP 160

170       180       190       200       210       220       230       240
          ....|....|....|....|....|....|....|....|....|....|....|....|....|....|....|....|
hCTL1_a-  KLPVPASAPIPFFHRCAPVNISCYAKFAEALITFVSDNSVLHRLISGVMTSKEIILGLCLLSLVLSMILMVIIRYISRVL 240
hCTL1_b-  KLPVPASAPIPFFHRCAPVNISCYAKFAEALITFVSDNSVLHRLISGVMTSKEIILGLCLLSLVLSMILMVIIRYISRVL 240

250       260       270       280       290       300       310       320
          ....|....|....|....|....|....|....|....|....|....|....|....|....|....|....|....|
hCTL1_a-  VWILTILVILGSLGGTGVLWWLYAKQRRSPKETVTPEQLQIAEDNLRALLIYAISATVFTVILFLIMLVMRKRVALTIAL 320
hCTL1_b-  VWILTILVILGSLGGTGVLWWLYAKQRRSPKETVTPEQLQIAEDNLRALLIYAISATVFTVILFLIMLVMRKRVALTIAL 320

330       340       350       360       370       380       390       400
          ....|....|....|....|....|....|....|....|....|....|....|....|....|....|....|....|
hCTL1_a-  FHVAGKVFIHLPLLVFQPFWTFFALVLFWVYWIMTLLFLGTTGSPVQNEQGFVEFKISGPLQYMWWYHVVGLIWISEFIL 400
hCTL1_b-  FHVAGKVFIHLPLLVFQPFWTFFALVLFWVYWIMTLLFLGTTGSPVQNEQGFVEFKISGPLQYMWWYHVVGLIWISEFIL 400

410       420       430       440       450       460       470       480
          ....|....|....|....|....|....|....|....|....|....|....|....|....|....|....|....|
hCTL1_a-  ACQQMTVAGAVVTYYFTRDKRNLPFTPILASVNRLIRYHLGTVAKGSFIITLVKIPRMILMYIHSQLKGKENACARCVLK 480
hCTL1_b-  ACQQMTVAGAVVTYYFTRDKRNLPFTPILASVNRLIRYHLGTVAKGSFIITLVKIPRMILMYIHSQLKGKENACARCVLK 480

490       500       510       520       530       540       550       560
          ....|....|....|....|....|....|....|....|....|....|....|....|....|....|....|....|
hCTL1_a-  SCICCLWCLEKCLNYLNQNAYTATAINSTNFCTSAKDAFVILVENALRVATINTVGDFMLFLGKVLIVCSTGLAGIMLLN 560
hCTL1_b-  SCICCLWCLEKCLNYLNQNAYTATAINSTNFCTSAKDAFVILVENALRVATINTVGDFMLFLGKVLIVCSTGLAGIMLLN 560

570       580       590       600       610       620       630       640
          ....|....|....|....|....|....|....|....|....|....|....|....|....|....|....|....|
hCTL1_a-  YQQDYTVWVLPLIIVCLFAFLVAHCFLSIYEMVVDVLFLCFAIDTKYNDGSPGREFYMDKVLMEFVENSRKAMKEAGKGG 640
hCTL1_b-  YQQDYTVWVLPLIIVCLFAFLVAHCFLSIYEMVVDVLFLCFAIDTKYNDGSPGREFYMDKVLMEFVENSRKAMKEAGKGG 640

650
          ....|....|....|..
hCTL1_a-  VADSRELKPMASGASSA 657
hCTL1_b-  VADSRELKPMLKKGR   654
```

FIGURE 10

CHOLINE TRANSPORT LIKE (CTL) MEMBRANE PROTEINS INVOLVED IN CHOLINE TRANSPORT

The present invention relates to the identification of a novel family of CTL (Choline Transporter Like) genes, in particular hCTL1 and hCTL2, involved in the metabolism and/or transport of choline in cells such as the intestinal tract cells, nervous cells, in particular motoneurons, sensitive neurons, neurons of the nucleus dorsalis of the spinal cord and oligodendrocytes. The invention opens up new prospects in particular for the treatment of familial dysautonomia, and Tangier disease. More generally, the identification of CTL genes enables new strategies for treating diseases of the nervous system, in particular neurodegenerative, demyelinating diseases, preferably Alzheimer's disease, Parkinson's disease and Huntington's disease to be developed.

Choline is a metabolite which contributes to the production of membranes via phosphatidylcholine. This metabolite also plays an important role in the cholinergic neurons where it participates in the synthesis of the neurotransmitter acetylcholine. In some cells, phosphatidylcholine may be produced by methylation of phosphatidylethanolamine, and in unicellular organisms, plants and animals, the free choline is absorbed as nutrient. The absorption of choline, which is dependent on sodium and coupled to the synthesis of acetylcholine in the cholinergic nerve endings, is particularly well characterized at the functional level (1-3), but has up until now eluded various tests of identification based on the purification of proteins (4) even together with the use of a selective and irreversible ligand.

In the context of the present invention, a choline transport mutation suppressor gene was cloned in yeast obtained from an expression library produced from the cDNA obtained from torpedo electric lobe. The homologous gene was then isolated in rats, rCTL1, which is highly expressed in the form of a 3.5 kb product of transcription in the spinal cord and the brain, and in the form of a 5 kb mRNA in the colon. In situ hybridization showed a high expression of rCTL1 in the motor, sensitive and nucleus dorsalis neurons of the spinal cord of rats and the oligodendrocytes, and to a lesser degree in various neuronal populations distributed throughout the brain. In peripheral tissues, high levels of rCTL1 have been identified in the cellular layer of the mucous membrane of the colon. In humans, the hCTL1 gene is associated with markers localized in 9q.31.2, close to the familial dysautonomia and Tangier disease loci. Several homologous genes have also been found in mammals (CTL2-4). The localization of hCTL2 in 19p13.1 and of hCTL4 in 6p21.3 indicates that the CTL proteins add to a number of other families of genes known to have been duplicated at these loci. All these genes homologous to CTL1 encode proteins comprising 10 putative transmembrane domains, of which 2 contain transporter type motifs. Thus, the identification and the characterization of this family of proteins, designated hereinafter CTL, opens up new prospects in particular for the treatment of familial dysautonomia, a disease which includes a peripheral cholinergic component (27) with both autonomous and motor manifestations at birth, and progressive demyelinization of the CNS in adults (28); and of Tangier disease (30) and (31). More generally, the identification of the CTL genes makes it possible to envisage new therapies for all the diseases involving the cells expressing the transcripts of a CTL gene such as the intestinal tract cells, nervous cells, in particular motoneurons, sensitive neurons, neurons of the nucleus dorsalis of the spinal cord and oligodendrocytes, in particular neurodegenerative, demyelinating diseases, Alzheimer's disease, Parkinson's disease and Huntington's disease.

DESCRIPTION

Thus, the present invention relates to a purified or isolated nucleic acid, characterized in that it comprises a nucleic sequence chosen from the group having the following sequences:
a) the sequence SEQ ID NO: 1 (hCTL1);
b) the sequence SEQ ID NO: 2 (hCT1.2);
c) a fragment of at least 12 consecutive nucleotides, preferably 15, 20, 30 or 50 consecutive nucleotides, of the sequence SEQ ID NO: 1 or 2;
d) a nucleic sequence exhibiting a percentage of overall identity of at least 608, preferably 80%, 90%, 95% or 99%, after optimal alignment with a sequence as defined in a), b) or c);
e) the complementary sequence or the RNA sequence corresponding to a sequence as defined in a), b), c) or d).

SEQ ID NO: 1 is the coding sequence for hCTL1 as represented below: GCTGCGCGCACGCGACCGCATC-CGGGCTCCTTCGGCCCCGCCATGGGCTGCTGCAGC TCCGCTTCCTCCGCCGCGCAGAGCTC-CAAACGAGAATGGAAGCCGCTGGAGGACCG TAGCTGCACAGACATACCATGGCTGCT-GCTCTTCATCCTCTTCTGCATTGGGATGGG ATT-TATTTGTGGCTTTTCAATAGCAACAGGT-GCAGCAGCAAGACTAGTGTCAGGATA CGACAGCTATGGAAATATCCGTGGGCA-GAAAAATACAAAGTTGGAAGCAATACCAA ACAGTGGCATGGACCACACCCAGCG-GAAGTATGTATTCTTTTTGGATCCATGCAACC TGGACTTGATAAACCGGAAGAT-TAAGTCTGTAGCACTGTGTGTAGCAGCGTGTCCAA GGCAAGAACTGAAAACTCTGAGTGATGT-TCAGAAGTTTGCAGAGATAAATGGTTCA GCCCTAT-GTAGCTACAACCTAAAGCCTTCTGAATA-CACTACATCTCCAAAATCTTCT GTTCTCTGCCCCAAACTACCAGTTC-CAGCGAGTGCACCTATTCCATTCTTCCATCGCT GTGCTCCTGTGAACATTTCCTGCTATGC-CAAGTTTGCAGAGGCCCTGATCACCTTTGT CAGT-GACAATAGTGTCTTACACAGGCTGATT-AGTGGAGTAATGACCAGCAAAGAAA TTATATTGGGACTTTGCTTGTTATCAC-TAGTTCTATCCATGATTTTGATGGTGATAAT CAGG-TATATATCAAGAGTACTTGTGTGGATCT-TAACGATTCTGGTCATACTCGGTTC ACTTGGAGGCACAGGTGTACTATGGTG-GCTGTATGCAAAGCAAAGAAGGTCTCCCA AAGAAACTGTTACTCCTGAGCAGCTTCA-GATAGCTGAAGACAATCTTCGGGCCCTCC TCATT-TATGCCATTTCAGCTACAGTGTTCA-CAGTGATCTTATTCCTGATAATGTTGGT TATGCGCAAACGTGTTGCTCTTAC-CATCGCCTTGTTCCACGTAGCTGGCAAGGTCTTC ATTCACTTGCCACTGCTAGTCTTCCAAC-CCTTCTGGACTTTCTTTGCTCTTGTCTTGTT TTGGGTGTACTGGATCATGACACT-TCTTTTTCTTGGCACTACCGGCAGTCCTGTTCAG AATGAGCAAGGCTTTGTGGAGT-TCAAAATTTCTGGGCCTCTGCAGTACATGTGGTGG TACCATGTGGTGGGCCTGATTTGGAT-CAGTGAATTTATTCTAGCATGTCAGCAGATG ACAGTGGCAGGAGCTGTGGTAACATAC- TATTTTACTAGGGATAAAAGGAATTTGCCA TTTA-
CACCTATTTTGGCATCAGTAAATCGCCT-
TATTCGTTACCACCTAGGTACGGTGG
CAAAAGGATCTTTCATTATCACATTAGT-
CAAAATTCCGCGAATGATCCTTATGTATA TTCA-
CAGTCAGCTCAAAGGAAAGGAAAATGCT-
TGTGCACGATGTGTGCTGAAATCTT
GCATTTGTTGCCTTTGGTGTCT-
TGAAAAGTGCCTAAATTATTTAAATCAGAATGCATA
CACAGCCACAGCTATCAACAGCAC-
CAACTTCTGCACCTCAGCAAAGGATGCCTTTGT
CATTCTGGTGGAGAATGCTTTGCGAGTG-
GCTACCATCAACACAGTAGGAGATTTTAT GTTAT-
TCCTTGGCAAGGTGCTGATAGTCTGCAG-
CACAGGTTTAGCTGGGATTATGCT
GCTCAACTACCAGCAGGACTACACAG-
TATGGGTGCTGCCTCTGATCATCGTCTGCCT
CTTTGCTTTCCTAGTCGCTCATTGCTTC-
CTGTCTATTTATGAAATGGTAGTGGATGTA TTAT-
TCTTGTGTTTTGCCATTGATACAAAATA-
CAATGATGGGAGCCCTGGCAGAGAAi
TTCtATATGGATAAAGTGCTGATG-
GAGTTTGTGGAAAACAGTAGGAAAGCAATGAA
AGAAGCTGGTAAGGGAGGCGTCGCTGAT-
TCCAGAGAGCTAAAGCCGATGCTGAAGA AAAGGT-
GACTGGTCTCATGAGCCCTGAAGAAT-
GAACTCAGAGGAGGTTGTTTACAT
GAGGTTCTCCCACTCACCAGCTGT-
TGAGAGTCTGCGATTATGAAGAGCAGGATCTTA
TTACTTCAATGAAAGCATGTAA-
CAAGTTTCTCAAACCACCAACAGCCAAGTGGATTT
GGTACAGTGCGGCTGTCTAATAAATAAT-
CAAAAGCATTTGATAGAAAAAAAAAAA The expression "hCTL1" will be understood to designate the gene encoding the two polypeptide forms derived from the alternative splicing CTL1a and CTL1b.

SEQ ID NO: 2 is the coding sequence for hCTL2 as represented below: GCGGCCGCCGGGGCTGGTCGCCT-
GCAGGGATGGGGGACGAGCGGCCCCACTACTAC
GGGAAACACGGAACGCCACAGAAGTAT-
GATCCCACTTTCAAAGGACCCATTTACAA
TAGGGGCTGCACGGATATCATATGCTGT-
GTGTTCCTGCTCCTGGCCATTGTGGGCTA CGTG-
GCTGTAGGCATCATAGCCTGGACTCATG-
GAGACCCTCGAAAGGTGATCTACCC
CACTGATAGCCGGGGCGAGTTCT-
GCGGGCAGAAGGGCACAAAAAACGAGAACAAA
CCCTATCTGTTTTATTTCAACATTGT-
GAAATGTGCCAGCCCCTGGTTCTGCTGGAAT
TCCAATGTCCCACTCCCCAGATCT-
GCGTGGAAAAATGCCCCGACCGCTACCTCACGT
ACCTGAATGCTCGCAGCTCCGG-
GACTTTGAGTACTATAAGCAGTTCTGTGTTCCTG
GCTTCAAGAACAATAAAGGAGTGGCT-
GAGGTGCTTCGAGATGGTGACTGCCCTGCT GTCCT-
CATCCCCAGCAAACCCTTGGCCCG-
GAGATGCTTCCCCGCTATCCACGCCTAC
AAGGGTGTCCTGATGGTGGGCAAT-
GAGACGACCTATGAGGATGGGCATGGCTCCCG
GAAAAACATCACAGACCTGGTG-
GAGGGCGCCAAGAAAGCCAATGGAGTCCTAGAG
GCGCGGCAACTCGCCATGCG-
CATATTTGAAGATTACACCGTCTCTTGG-
TACTGGATT ATCATAGGCCTGGTCATTGCCATGGC-
GATGAGCCTCCTGTTCATCATCCTGCTTCGCT
TCCTGGCTGGTATTATGGTCTGGGTGAT-
GATCATCATGGTGATTCTGGTGCTGGGCTA CGGAATATTTCACTGCTACATGGAG-
TACTCCCGACTGCGTGGTGAGGCCGGCTCTGA
TGTCTCTTTGGTGGACCTCGGCTTTCA-
GACGGATTTCCGGGTGTACCTGCACTTACGG
CAGACCTGGTTGGCCTTTATGATCAT-
TCTGAGTATCCTTGAAGTCATTATCATCTTGC TGCT-
CATCTTTCTCCGGAAGAGAATTCT-
CATCGCGATTGCACTCATCAAAGAAGCCA
GCAGGGCTGTGGGATACGTCATGTGCTC-
CTTGCTCTACCCACTGGTCACCTTCTTCTT GCTGT-
GCCTCTGCATCGCCTACTGGGCCAG-
CACTGCTGTCTTCCTGTCCACTTCCAAC
GAAGCGGTCTATAAGATCTTTGATGA-
CAGCCCCTGCCCATTACTGCGAAAACCTGC AAC-
CCAGAGACCTTCCCCTCCTCCAAT-
GAGTCCCGCCAATGCCCCAATGCCCGTTGC
CAGTTCGCCTTCTACGGTGGT-
GAGTCGGGCTACCACCGGGCCCT-
GCTGGGCCTGCAG ATCTTCAATGCCTTCATGTTCT-
TCTGGTTGGCCAACTTCGTGCTGGCGCTGGGCCAG
GTCACGCTGGCCGGGGCCTTTGCCTC-
CTATTACTGGGCCCTGCCGCAAGCCGGACGACC
TGCCGGCCTTCCCGCTCTTCTCTGC-
CTTTGGCCGGGCGCTCAGGTACCACACAGGCT
CCCTGGCCTTTGGNGCGCTCATCCTGGC-
CATTGTGCAGATCATCCGTGTGATACTCG AGT-AC-
CTGGATCAGCGGCTGAAAGGTGCA-
GAGAACAAGTTTGCCAAGTGCCTCATG
ACCTGTCTCAAATGCTGCTTCTGGTGC-
CTGGAGAAGTTCATCAAATTCCTTAATAGG AATGC-
CTACATCATGATTGCCATCTACGGCAC-
CAATTTCTGCACCTCGGCCAGGAAT
GCCTTCTTCCTGCTCATGAGAAACAT-
CATCAGAGTGGCTGTCCTGGATAAAGTTACT GACT-
TCCTCTTCCTGTTGGGCAAACTTCT-
GATCGTTGGTAGTGTGGGGATCCTGGCTT
TCTTCTTCTTCACCCACCGTATCAG-
GATCGTGCAGGATACAGCACCACCCCTCAATT
ATTACTGGGTTCCTATACTGACGGT-
GATCGTTGGCTCCTACTTGATTGCACACGGTTT
CTTCAGCGTCTATGGCATGTGTGTGGA-
CACGCTGTTCCTCTGCTTCTTGGAGGACCTG
GAGAGGAATGACGGCTCGGCCGAGAGGC-
CTTACTTCATGTCTTCCACCCTCAAGAA ACTCT-
TGAACAAGACCAACAAGAAGGCAGCG-
GAGTCCTGAAGGCCCCGTGCTCCCC
ACCTCTCAAGGAGTCTCATGCCG-
CAGGGTGCTCAGTAGCTGGGTCTGTTCCCCCAGC
CCCTTGGGTTCACCTGAAGTCCTAT-
CACTGCCGCTCTGCCCCTCCCCATGAGCCAGA
TCCCACCAGTTTCTGGACGTG-
GAGAGTCTGGGGCATCTCCTTCTTATGC-
CAAGGGGC GCTTGGAGTTTTCATGGCTGCCCCTC-
CAGACTGCGAGAAACAAGTAAAAACCCWTT
GGGGCCTCTTGATGTCTGGGATG-
GCACGTGGCCCGACCTCCACAAGCTCCCTCATGC
TTCCTGTCCCCCGCTTACACGA-
CAACGGGCCAGACCACAGGAAGGACGGT-
GTTTGTG TCTGAGGGAGCTGCTGGCCACAGTGAA-
CACCCACGTTTATTCCTGCCTGCTCCGGCC
AGGACTGAACCCCTTCTCCACACCTGAA-
CAGTTGGCTCAAGGGCCACCAGAAGCATT TCTT-
TATTATTATTATTTTTTAACCTGGACAT-
GCATTAAAGGGTCTATTAGCTTTCTTT
YNCGTCTGTCTCAACAGCTGANAT-
NGGGGCCGCCAAGGAGTGCCTTTCCTTTTGCTT

CCTTCNTAGGTTGGAGTTAACGGGTGG-
GAAGTTTTTTTTCCCANGTGGGGGTGTTTTC CTG-
GTTGGGAAGG

The terms nucleic acid, nucleic sequence or nucleic acid sequence, polynucleotide, oligonucleotide, polynucleotide sequence and nucleotide sequence, terms which will be used indifferently in the present description, will be understood to designate a precise succession of nucleotides, modified or otherwise, which make it possible to define a fragment or a region of a nucleic acid, containing or otherwise non-natural nucleotides, and which may correspond to a double-stranded DNA, a single-stranded DNA and the products of transcription of said DNAs. A natural nucleotide of a nucleic acid is defined in that the nitrogen base is chosen from adenine, guanine, uracil, cytosine, and thymine. A nucleotide may be modified on the bases. There may be mentioned in particular inosine, 5-methyldeoxycytidine, deoxyuridine, 5-dimethylaminodeoxyuridine, 2,6-diaminopurine, 5-bromodeoxyuridine or any other modified base capable of hybridization.

It should be understood that the present invention does not relate to nucleotide sequences in their natural chromosomal environment, that is to say in the natural state. They are sequences which have been isolated and/or purified, that is to say that they have been removed directly or indirectly, for example by copying, their environment having been at least partially modified.

The expression "percentage of overall identity" between two nucleic acid or amino acid sequences for the purposes of the present invention is understood to designate a percentage of identical nucleotides or amino acid residues between the two complete sequences to be compared, which is obtained after the best alignment, this percentage being purely statistical and the differences between the two sequences being distributed randomly and over their entire length. Sequence comparisons between two nucleic acid or amino acid sequences are traditionally carried out by comparing these complete sequences after they have been optimally aligned, said comparison being carried out by segment or by "comparison window" in order to identify and compare the local regions of sequence similarity. The optimal alignment of sequences for the comparison may be carried out, as well as manually, by means of the local homology algorithm of Smith and Waterman (1981) [Ad. App. Math. 2: 482], by means of the local homology algorithm of Neddleman and Wunsch (1970) [J. Mol. Biol. 48: 443], by means of the Pearson and Lipman similarity search method (1988) [Proc. Natl. Acad. Sci. USA 85: 2444], by means of computer software using these algorithms (GAP, BESTFIT, FASTA and TFASTA in the Wisconsin Genetics Software Package, Genetics Computer Group, 575 Science Dr., Madison, Wis.) and (DNASIS, Version 2.5 for Windows; Hitachi Software Engineering Co., Ltd, South San Francisco, Calif., using the standard parameters described in the manufacturer's manual).

In this context, the sequences and the percentage identity may also be obtained using internet computer resources. Mention may be made of the Blast programs, available from the NCBI web site, and the FastDB program with the following parameters "Mismatch penalty 1.00; Gap Penalty 1.00; Gap Size Penalty 0.33; joining penalty 30.0. These algorithms are presented in Current Methods in Sequencing and synthesis Methods and Applications, pages 127-149, 1988, Ala R. Liss, Inc.

The percentage identity between two nucleic acid or amino acid sequences is determined by comparing these two optimally aligned sequences by "comparison window" in which the region of the nucleic acid or amino acid sequence to be compared may comprise additions or deletions relative to the reference sequence for an optimal alignment between these two sequences. The percentage identity is calculated by determining the number of identical positions for which the nucleotide or amino acid residue is identical between the two sequences, by dividing this number of identical positions by the total number of positions in the comparison window and by multiplying the result obtained by 100 in order to obtain the percentage identity between these two sequences.

The expression nucleic sequences exhibiting a percentage identity of at least 60%, preferably 80%, 90% 95% or 99%, after optimal alignment with a reference sequence, will be understood to designate the nucleic sequences having, compared with the reference nucleic sequence, certain modifications such as in particular a deletion, truncation, extension, chimeric fusion and/or substitution, in particular which is localized at a point, and whose nucleic sequence exhibits at least 60%, preferably 80%, 90%, 95% or 99%, identity after optimal alignment with the reference nucleic sequence. They are preferably sequences whose complementary sequences are capable of specifically hybridizing with the sequence SEQ ID NO: 1 or 2 of the invention. Preferably, the specific or high stringency hybridization conditions are such that they allow at least 60%, preferably 80%, 90%, 95% or 99%, identity after alignment between one of the two sequences and the sequence complementary to the other.

Hybridization under high stringency conditions means that the temperature and ionic strength conditions are chosen such that they allow the hybridization to be maintained between two complementary DNA fragments. By way of illustration, high stringency conditions of the hybridization step for the purposes of defining the polynucleotide fragments described above are advantageously the following. DNA-DNA or DNA-RNA hybridization is carried out in two steps: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% formamide, 7% sodium dodecyl sulfate (SDS), 10× Denhardt's, 5% dextran sulfate and 1% salmon sperm DNA; (2) actual hybridization for 20 hours at a temperature dependent on the size of the probe (i.e.: 42° C., for a probe having a size>100 nucleotides) followed by 2 washes of 20 minutes at 20° C. in 2×SSC+2% SDS, 1 wash of 20 minutes at 20° C. in 0.1×SSC+0.1% SDS. The final wash is performed in 0.1×SSC+0.1% SDS for 30 minutes at 60° C. for a probe having a size>100 nucleotides. The high stringency hybridization conditions described above for a polynucleotide of defined size will be adapted by persons skilled in the art for larger or smaller sized oligonucleotides according to the teaching of Sambrook et al. Molecular Cloning A Laboratory Manual (Cold Spring Harbor Press, 1989) in paragraphs 11.1 to 11.61.

Among the nucleic sequences exhibiting a percentage of overall identity of at least 60%, preferably 80%, 90%, 95% or 99%, after optimal alignment with the sequence according to the invention, the variant nucleic sequences of the nucleic sequence SEQ ID NO: 1 or 2, or fragments thereof, that is to say all the nucleic sequences corresponding to allelic variants, that is to say individual variations of the nucleic sequence SEQ ID NO: 1 or 2, are also preferred. These natural mutated sequences correspond to polymorphisms present in mammals, in particular in human beings and, in particular, to polymorphisms which may lead to the onset of a pathology. Preferably, the present invention relates to variant nucleic sequences in which the mutations lead to a modification of the amino acid sequence of the polypeptide, or of fragments thereof, encoded by the normal sequence having the sequence SEQ ID NO: 1 or 2.

Preferably, the nucleic acid according to the invention consists of the sequence SEQ ID No. ID NO: 1 the complementary sequence or of the corresponding RNA sequence of the sequence SEQ ID NO: 1 or of the sequence SEQ ID NO: 2, the complementary sequence or of the corresponding RNA sequence of the sequence SEQ ID NO: 2. Said nucleic acid may contain any coding sequence for a polypeptide selected from hCTL1 having the sequence SEQ ID NO: 3, hCTL1a having the sequence SEQ ID No. 9 and hCTL2 having the sequence SEQ ID NO: 4.

A second aspect of the invention relates to a polypeptide, characterized in that it comprises a peptide sequence having at least 80%, preferably 90%, 95% or 99%, identity after optimal alignment with a sequence selected from SEQ ID NO: 3, 4 and 9, said polypeptide being involved in the metabolism and/or the transport of choline in the cells, in particular in the nervous cells.

Preferably, said polypeptide possesses a sequence selected from SEQ ID NO. 3, 4 and 9.

The following sequence SEQ ID NO: 3 represents the polypeptide hCTL1b: MGCCSSASSAAQSSKREWK-PLEDRSCTDIPWLLLFILFCIGMGFICG-FSIATGAAARLVSG YDSYGNIRGQKNTKLEAIPNSG-MDHTQRKYVFFLDPCNLDLINRKIKSVAL CVAACPRQE LKTLSDVQKFAEINGSALCSYNLKP-SEYTTSPKSSVLCPKLPVPASAPIPFFHRCAPVNISC YAKFAEALITFVSDNSVLHRLIS-GVMTSKEIILGLCLLSLVLSMILMVIIR-YISRVLVWILTIL VILGSLGGTGVLWWLYAKQRRSP-KETVTPEQLQIAEDNLRALLIYAISATVFTVILFLIML VMRKRVALTIALFHVAGKVFIHL-PLLVFQPFWTFFALVLFWVYWIMTLLFLGTTGSPVQ NEQGFVEFKISGPLQYMWWYHVVGLI-WISEFILACQQMTVAGAVVTYYFTRDKRNLPFT PILASVNRLIRYHLGTVAKGSFI-ITLVKIPRMILMYIHSQLKGKENAC-ARCVLKSCICCLWC LEKCLNYLNQNAYTATAINSTN-FCTSAKDAFVILVENALRVATINTVGDFMLFLGKVLIV CSTGLAGIMLLNYQQDYTVWVLPLIIV-CLFAFLVAHCFLSIYEMVVDVLFLCFAIDTKYN DGSPGREFYMDKVLMEFVENSRKA-MKEAGKGADSRELKPMLKKR SEQ ID NO: 9 (hCTL1a) corresponds to another form derived from an alternative splicing of the hCTL1 gene. It differs from hCTL1b only in its C-terminal end. The sequences preceding the stop codon are respectively MLKKR (residues 650-654 of SEQ ID NO: 3) for hCTL1b and MASGASSA (residues 650-657 of SEQ ID NO: 9) for hCTL1a (FIG. 10). Unless otherwise stated, the expression hCTL1 protein or polypeptide will be understood to denote both hCTL1a and hCTL1b.

The following sequence SEQ ID NO: 4 represents the polypeptide hCTL2: MGDERPHYYGKHGTPQKYDPT-FKGPIYNRGCTDIICCVFLLLAIVGY-VAVGIIAWTHGDP RKVIYPTDSRGEFCGQKGTKNEN-KPYLFYFNIVKCASPLVLLEFQCPTPQICVEKCPDRYL TYLNARSSRDFEYYKQFCVPGFKNNKG-VAEVLRDGDCPAVLIPSKPLARRCFPAIHAYK GVLM-VGNETTYEDGHGSRKNITDLVEGAK-KANGVLEARQLAMRIFEDYTVSWYWIIIGL VIAMAMSLLFIILLRFLAGIMVWVMIIM-VILVLGYGIFHCYMEYSRLRGEAGSDVSLVDL GFQT-DFRVYLHLRQTWLAFMIILSILEVII-ILLLIFLRKRILIAIALIKEASRAVGYVMCSLLY PLVTFFLLCLCIAYWASTAV-FLSTSNEAVYKIFDDSPCPFTAKTCN-PETFPSSNESRQCPN ARCQFAFYGGESGYHRALLGL-QIFNAFMFFWLANFVLALGQVTLAGAFASY YWALRKP DDLPAFPLFSAFGRALRYHTGSLAFVA-LILAIVQIIRVILEYLDQRLKGAENKFAKCLMTC LKC-CFWCLEKFIKFLNRNAYIMIAIYGTN-FCTSARNAFFLLMRNIIRVAVLDKVTDFLFLL GKLLIVGSVGILAFFFFTHRIRIVQD-TAPPLNYYWVPILTVIVGSYLIAHGFFSVYGMCVDT LFLCFLEDLERNDGSAERPY-FMSSTLKKLLNKTNKKAAES These polypeptides are characterized in that their substrate is choline. In this sense, they are involved in the production of acetylcholine and/or in the production of the phospholipid components of the membrane of cells, in particular of intestinal tract cells, nervous cells such as motoneurons, sensitive neurons, neurons of the nucleus dorsalis of the spinal cord and oligodendrocytes.

Another aspect of the invention relates to a vector comprising a nucleotide sequence as defined above. In this vector, said sequence may be fused with a promoter which is effective in eukaryotic and/or prokaryotic cells and/or may additionally comprise a selectable gene. Thus, a cell transformed with said vector is also included. Among the cells which may be transformed, there may of course be mentioned bacterial cells (Olins and Lee, 1993), but also yeast cells (Buckholz, 1993), as well as animal cells, in particular mammalian cell cultures (Edwards and Aruffo, 1993), and in particular Chinese hamster ovary (CHO) cells, but also insect cells in which it is possible to use methods using baculoviruses for example (Luckow, 1993).

The invention also relates to an antibody capable of binding specifically to a polypeptide mentioned above.

An additional aspect of the invention relates to a method allowing the amplification and/or detection of a nucleic acid defined above in a sample, characterized in that at least one oligonucleotide comprising at least 12 consecutive nucleotides, preferably 15, 20, 30 or 50 consecutive nucleotides, having a sequence indicated above or having a sequence capable of hybridizing thereto is used as primer and/or probe. Advantageously, such a sequence is capable of specifically recognizing hCTL1a, hCTL1b and hCTL2.

The invention also relates to a method for identifying other genes belonging to the family of CTL genes, characterized in that there is used as primer and/or probe at least one oligonucleotide comprising at least 12 consecutive nucleotides, preferably 15, 20, 30 or 50 consecutive nucleotides, having the sequence indicated above or a sequence capable of hybridizing thereto.

This method may be carried out in order to identify CTL genes in various tissues in different animal species, in particular in mammals, in particular in humans.

It can also serve to isolate and to characterize the non-coding regions of the CTL genes mentioned above, in particular hCTL1 and hCTL2.

Such a method makes it possible to identify one or more mutations in the coding or noncoding regions CTL genes linked to genetic diseases involving nervous cells, in particular familial dysautonomia, and Tangier disease; and neurodegenerative, demyelinizing diseases, preferably Alzheimer's disease, Parkinson's disease and Huntington's disease.

The expression "mutations" is understood to mean deletions, insertions and point mutations which may be in both the coding and noncoding regions of the CTL genes (intron, promoter, enhancer or silencer). Thus, it is possible to identify mutations affecting the activity of the CTL protein, the splicing of the gene and its level of expression.

A "probe" is defined, for the purposes of the invention, as being a nucleotide fragment comprising, for example, from 12 to 100 nucleotides, in particular from 15 to 35 nucleotides, possessing a specificity of hybridization under defined conditions for forming a hybridization complex with a target nucleic acid. The probes according to the invention, whether they are specific or nonspecific, may be immobilized, directly or indirectly, on a solid support; reference is then made to "capture probe". Moreover, said probes may carry a marker agent allowing their detection; reference is then made to "detection probe".

A "capture probe" is immobilized or can be immobilized on a solid support by any appropriate means, for example by covalent bonding, by adsorption, or by direct synthesis on a solid support. These techniques are in particular described in patent application WO 92/10092. The most general method consists in immobilizing the nucleic acid extracted from the cells of various tissues or cells in culture on a support (such as nitrocellulose, nylon, polystyrene) and in incubating, under well-defined conditions, the target nucleic acid immobilized with the probe. After hybridization, the excess probe is removed and the hybrid molecules formed are detected by the appropriate method (measurement of the radioactivity, of the fluorescence or of the enzymatic activity linked to the probe). There may also be mentioned, as solid support, DNA chips, in particular the chips marketed by Affymetrix, Cis Bio International/LETI.

A "detection probe" may be labeled by means of a marker chosen for example from radioactive isotopes, enzymes, in particular enzymes capable of acting on a chromogenic, fluorigenic or luminescent substrate (in particular a peroxidase or an alkaline phosphatase), chromophoric chemical compounds, chromogenic, fluorigenic or luminescent compounds, nucleotide base analogs, and ligands such as biotin. The labeling of the primers or of the probes according to the invention is carried out by radioactive elements or by nonradioactive molecules. Among the radioactive isotopes used, there may be mentioned 32P, 33P, 35S, 3H or 125I. The nonradioactive entities are selected from ligands such as biotin, avidin, streptavidin, dioxygenin, haptens, dyes, luminescent agents such as radioluminescent, chemiluminescent, bioluminescent, fluorescent and phosphorescent agents.

The polynucleotides according to the invention may thus be used as primer and/or probe in methods using in particular the PCR (polymerase chain reaction) technique (Erlich, 1989; Innis et al., 1990, and Rolfs et al., 1991). This technique requires the choice of pairs of oligonucleotide primers delimiting the fragment which should be amplified. Reference may be made, for example, to the technique described in American patent U.S. Pat. No. 4,683,202. The amplified fragments may be identified, for example, after agarose or polyacrylamide gel electrophoresis, or after a chromatographic technique such as gel filtration or ion-exchange chromatography, and then sequenced. The specificity of the amplification may be checked using, as primer, the nucleotide sequences of polynucleotides of the invention as template, plasmids containing these sequences or alternatively the derived amplification products. The amplified nucleotide fragments may be used as reagents in hybridization reactions in order to demonstrate the presence; in a biological sample, of a target nucleic acid having a sequence complementary to that of said amplified nucleotide fragments. As a general rule, depending on the length of the oligonucleotides used, the temperature for the hybridization reaction is between about 25 and 65° C., in particular between 35 and 65° C. in a saline solution at a concentration of about 0.8 to 1 M. As regards the specific probes, the pairing may take place at temperatures above 50° C. for 1 to 2 mM MgCl2. The temperature for hybridization of an oligonucleotide being calculated on the basis of 2° C. per A or T and of 4° C. for G or C; an oligonucleotide consisting, for example, of a combination of 7 A and 5 C hybridizes at 34° C. This rule, which is well known to persons skilled in the art, makes it possible to calculate the hybridization temperature which can be envisaged for all the oligonucleotides according to the invention.

Other techniques for amplifying the target nucleic acid may be advantageously used as alternatives to PCR (PCR-like) with the aid of a pair of primers having nucleotide sequences according to the invention. The expression PCR-like will be understood to designate all the methods using direct or indirect reproductions of the nucleic acid sequences, or alternatively in which the labeling systems have been amplified; these techniques are well known; in general they include the amplification of DNA by a polymerase; when the original sample is an RNA, it is advisable to carry out a reverse transcription beforehand. There are currently a very large number of methods allowing this amplification, such as for example the SDA (Strand Displacement Amplification) technique (Walker et al., 1992), the TAS (Transcription-based Amplification System) technique described by Kwoh et al. in 1989, the 3SR (Self-Sustained Sequence Replication) technique described by Guatelli et al. in 1990, the NASBA (Nucleic Acid Sequence Based Amplification) technique described by Kievitis et al. in 1991, the TMA (Transcription Mediated Amplification) technique, the LCR (Ligase Chain Reaction) technique described by Landegren et al. in 1988 and perfected by Barany et al. in 1991, which uses a thermostable ligase, the RCR (Repair Chain Reaction) technique described by Segev in 1992, the CPR (Cycling Probe Reaction) technique described by Duck et al. in 1990, the Q-beta-replicase amplification technique described by Miele et al. in 1983 and perfected in particular by Chu et al. in 1986 and Lizardi et al. in 1988, and then by Burg et al. and by Stone et al. in 1996.

In the case where the target polynucleotide to be detected is an mRNA, there will be advantageously used, prior to the carrying out of an amplification reaction with the aid of the primers according to the invention or to the use of a method of detection with the aid of the probes of the invention, a reverse transcriptase-type enzyme in order to obtain a cDNA from the mRNA contained in the biological sample. The cDNA obtained will then serve as a target for the primers or the probes used in the method of amplification or of detection according to the invention. As indicated above, probes or primers which can discriminate between hCTL1a, hCTL1b and hCTL2 are particularly targeted by the invention.

The invention also relates to a diagnostic kit, characterized in that it makes it possible to carry out the method described above.

The invention also relates to the use of CTL4 whose peptide and nucleotide sequence is available in genbak under the accession number AF1347726 and GI number: 4529886 (sequence called NG22) in the context of the methods detailed in the description.

An additional aspect of the invention consists in a method for screening compounds capable of modifying the activity of a polypeptide described above.

This method may be characterized in that it comprises the following steps:

a) expression of said polypeptide in a host cell using a vector according to the invention,
b) incubation of the host cell obtained in step a) with choline and/or a choline analog labeled with an isotope, in particular with choline analogs such as HC-3, HC-15, d-tubocurarine, oxotremorine or carbamyl-b-methylcholine and at least one compound capable of modifying the activity of said polypeptide,
c) detection of the incorporation of choline and/or analysis of the quantity of acetylcholine produced.

Of course, any variant or any other technique which makes it possible to identify and to select compounds capable of modifying the activity of the CTL proteins is a subject of the invention. In this sense, the use of the CTL genes and proteins to identify and to select compounds capable of modifying their activity is particularly targeted.

This method allows the identification of a compound capable of restoring the activity of a polypeptide comprising at least one mutation identified by means of the method mentioned above. It also allows the identification of a compound capable of inhibiting the activity of a polypeptide according to the invention.

This method of screening allowing the identification of compounds acting on the activity of CTLs may be illustrated by the following examples which may be carried out during routine experiments by persons skilled in the art (O'Regan S. Binding of [3H]Hemicholinium-3 to the high affinity choline transporter in Electric Organ Synaptosomal Membranes, J. of Neurochemistry, 1988, Vol 51, No. 6, 1682: 1687):

The [3H]hemicholinium (HC-3) ligand can serve as marker for the activity of the high affinity choline transport system closely associated with the synthesis of acetylcholine (ACh) in the cholinergic nerve endings (Kuhar and Murrin, 1978; Jope; 1979). It indeed allows the characterization and the localization of the [3H]HC-3 binding sites in the membranes of rat nerve cells (Vickroy et al., 1984b; Sandberg et Coyle, 1985; Chatterjee et al., 1987) and the monitoring of the modifications which occur after lesions (Vickroy et al., 1984a), after various treatments with compounds, in particular with medicaments (Swann et al., 1986; Lowenstein and Coyle, 1986), or under depolarization conditions (Saltarelli et al., 1987) known to modify other presynaptic cholinergic parameters.

Thus, in the context of the invention, it is possible to measure the effect of compounds on the activity of the CTL polypeptides in the transport of choline in the synaptosomes.

To this effect, it is possible to measure the capture of choline in aliquot fractions of synaptosomes containing [3H]choline (15 Ci/mmol, CEA, Saclay, France). Nonlabeled choline is added for the determination of the transport parameters. At the end of the incubation period, the mixture is centrifuged and the pellet is recovered in 50 µl of Triton X-100 at 10%. The tubes are rinsed once and the samples and the rinsing liquids are transferred into counting flasks filled with 5 ml of Ready Protein scintillation fluid (Beckman, Palo Alto, Calif., U.S.A.). The radioactivity is determined using a Beckman LS3801 type counter for example.

The kinetic parameters of the transport of choline in the high affinity range are estimated using a nonlinear least-squares regression analysis (Jolivet, 1982) to adjust a simple Michaelis-Menten function at the experimental data, or Lineweaver-Burk and Scatchard representations with a linear regression program. Log-logit curves are used to determine the IC50 values for choline (Sigma, St. Louis, Mo., U.S.A.), choline analogs, HC-3, HC-15 (Aldrich, Steinheim, Germany), d-tubocurarine (Serva, Heidelberg, Germany), oxotremorine (Sigma), and carbamyl-b-methylcholine (Sigma).

It is also possible measured the binding of HC-3 to the membranes. A rapid centrifugation technique is used to separate the bound ligand from the free ligand in this method in order to reduce the loss of bound ligand to the minimum and to facilitate comparisons between the various preparations. Aliquot fractions (2511) of membranes in Tris buffer (10 mM, pH 8.0) are mixed with 75 µl of 0.4 M NaCl, 10 mM glycylglycine, pH 7.1, in order to determine total binding, or alternatively of 0.4 M LiCl, 10 mM glycylglycine, pH 7.1, in order to determine binding independent of Na; in both cases, the final salt concentration is 300 mM at pH 7.4, similar to that of the binding medium recommended by Sandberg and Coyle (1985). The equilibrium is reached at the end of 5 min of incubation and the quantity of [3H]HC-3 bound is proportional to the quantity of membranes added in the interval ranging from 10 to 100 µg of proteins. Generally, membranes containing about 40 µg of proteins at room temperature (20-22° C.) are incubated for 15 min with 10 nM of [3H]HC-3 (132.8 Ci/mmol, New England Nuclear, Boston, Mass., U.S.A.) in ultratransparent airfuge tubes (Beckman). The samples are then centrifuged for 5 min, in a Beckman airfuge at 100 psi (55 000 gmax.). The supernatants are collected and the sides and the bottoms of the tubes are wiped without disturbing the pellets. The pellets are then resuspended in 50 µl of 10% Triton X-100, and they are then transferred into counting flasks, with 50 µl of aqueous rinsing solution, for the determination of the radioactivity. The binding parameters are thus determined using total synaptosomal membranes and a [3H]HC-3 concentration range (5-120 nM), and a nonlinear regression analysis is carried out in order to adjust the function $B=(B_{max} \times F)/(K_D+F)$ at the experimental data (where B is the bound ligand and F is the free ligand), after subtraction of the Na-independent binding or using Scatchard representations. In some cases, it is possible to measure the blank values in the presence of 100 µM of nonlabeled choline.

The apparent number of rotations for the choline transporter may be calculated by dividing the Vmax for the transport of choline of high affinity by the Bmax for the HC-3 binding sites. The two parameters are determined using a material obtained from the same preparation of synaptosomes. The data are normalized relative to the recovery of AChE in the final pellets of samples treated in parallel, because the protein content of the synaptosomes and that of the synaptosomal membranes differ because of the contribution of the cytoplasmic proteins to the protein content.

The subject of the invention is also a compound capable of being obtained from the method described above and a composition comprising said compound or a vector previously detailed and a pharmaceutically acceptable vehicle.

Thus, one aspect of the invention relates to the use of said compound or vector for the manufacture of a medicament, in particular a medicament intended for the treatment of genetic diseases involving cells expressing the transcripts of a CTL gene such as intestinal tract cells, nervous cells in the broad sense, in particular motoneurons, sensitive neurons and oligodendrocytes, in particular familial dysautonomia, and Tangier disease or alternatively a medicament intended for the treatment of diseases of nervous origin, in particular anxiety, nervousness, anguish, behavioural, vigilance, memory and sleep disorders, and neurodegenerative, demyelinizing diseases, preferably Alzheimer's disease, Parkinson's disease and Huntington's disease. A close correlation in fact exists between Alzheimer's disease and the quantity of acetylcholine transferase (Baskin D. S et al Arch Neurol, 1999, Sep.; 56(9) 1121: 1123) or the self-inhibitory action of endogenous acetylcholine in the brain of patients (Albrecht C et al, Exp brain Res 1999 128(3) 383: 389, demonstrating the involvement of the metabolism and the transport of choline in this disease.

Thus, a clone was isolated from an expression library prepared from torpedo electric lobe DNA, said clone being capable of suppressing a mutation of choline transport in yeast. High levels of expression of the homolog are found in rats, rCTL1, in the motor neurons and the oligodendrocytes, but lower levels of expression also appear in neuronal populations dispersed in the brain. Thus, the distribution of rCTL1s in the CNS is not only limited to what is expected for a cholinergic protein. In addition, a 5 kb mRNA is associated with a high expression in the cellular layer of the mucous membrane of the colon. The cholinergic neurons are particularly sensitive to modifications in the metabolism of choline because they require choline for the synthesis both of the membrane and of the neurotransmitter (25, 26). The CTL proteins can therefore provide the choline for the synthesis of the components of the membrane and/or may be involved in the synthesis of acetylcholine. The expression of tCTL1 and rCTL1 in the form of complete coding sequences in oocytes and in various cultured cells shows significant modifications in the absorption of choline.

The CTL family is characterized by 10 putative transmembrane domains and 11 highly conserved cysteines. These proteins share a limited structural homology with the transporters, and in particular with the transmembrane domains TNM 2 and 3 (see FIG. 2D). Plants and simple animals, such as *C. elegans*, have only one gene of this nature (FIG. 2E). On the other hand, it is clear that human beings and mice have 15 three or probably four different homologous genes situated in chromosomal positions where numerous duplicated genes are found. The chromosomal localization of hCTL1 in the vicinity of D9S299 in 9g31.2 places this gene in close proximity with the loci responsible for genetic diseases such as familial dysautonomia and Tangier disease. The high expression of rCTL1 in the motor neurons, sensitive neurons and 20 oligodendrocytes, and the functional relationship with the absorption of choline make it a promising candidate for the site of mutation causing familial dysautonomia, a disease which includes a peripheral cholinergic component (27) with both autonomous and motor manifestations at birth, and gradual demyelinization of the CNS in adults (28). Current efforts to refine the genomic localization of hCTL1 combined with the recent narrowing of the range of markers adjacent to the locus associated with functional dysautonomia (29) indicate that the exonic region of hCTL1 is close, but proximal, to the site of mutation, leaving the possibility of a permutation in the regulatory domain in 5'.

The Tangier disease mutation is less well localized and hCTL is in the range of markers associated with this disease. In Tangier disease, reduced levels of high-density lipoproteins result in a low level of circulating cholesterol with a recurrent neuropathy and an intestinal lipid storage (30). It is known that choline, via phosphatidylcholine, is involved in the production of high-density lipoproteins. In this sense, it has been shown that lecithin, a phospholipid synthesized from choline, increases bile secretion of high-density lipoproteins (31).

The identification of this new family of proteins in humans therefore opens the way for the development of pharmacological tools which could be useful for the treatment of various diseases linked to disruptions in the CTL functions, in particular at the level of cells such as intestinal tract cells, nerve cells, in particular motoneurons, sensitive neurons, neurons of the nucleus dorsalis of the spinal cord and oligodendrocytes.

Reference will be made to the legends to the figures presented below for the remainder of the description.

LEGENDS

Figure 1B:
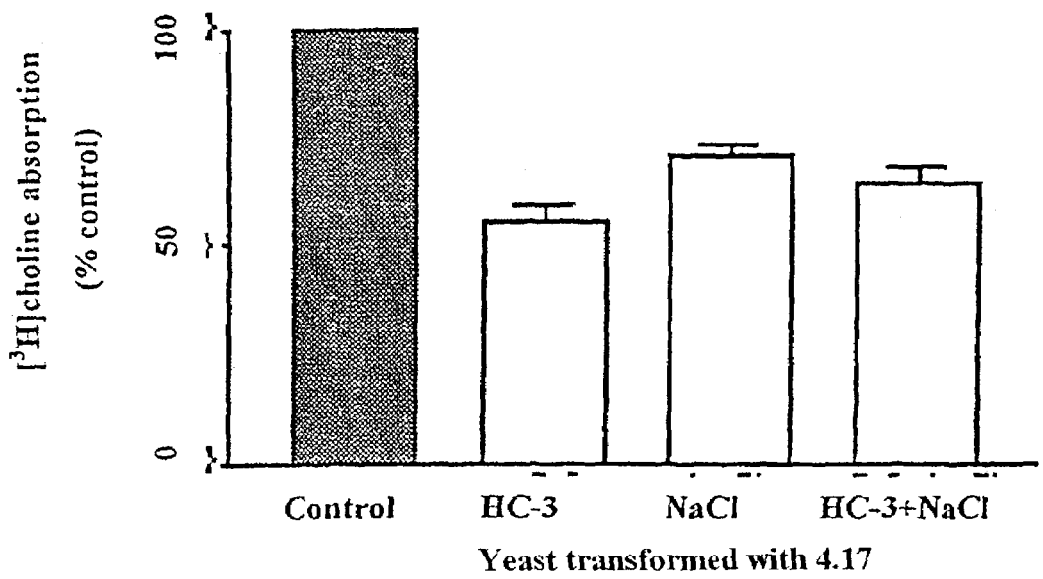

FIGS. 1A-1B: Suppression of the choline transport mutations in yeast by heterologous expression of electric lobe cDNA.

(A) Mutant yeasts are transformed with individual plasmids isolated from colonies exhibiting choline-dependent growth under selective conditions. The transformed yeast was incubated at 30° C. for 30 minutes with 25 nM [3H]-choline. The saturable choline absorption was measured in the form of the difference in absorption in the presence and in the absence of 1 mM cold choline, and the measurement was normalized in order to take growth into account (OD600); 4.16 is a plasmid without insert and it was used as control. Only 4.17 has the capacity to induce the absorption of choline (mean (standard deviation for 3-5 independent experiments).

(B) Characterization of the absorption of choline by the mutant yeast transformed by 4.17. The absorption of choline was inhibited to a similar extent with 1 μM HC-3 by the addition of 100 mM NaCl, and by the addition of HC-3 as for NaCl (mean (standard deviation for 5 independent experiments).

Figure 2A:
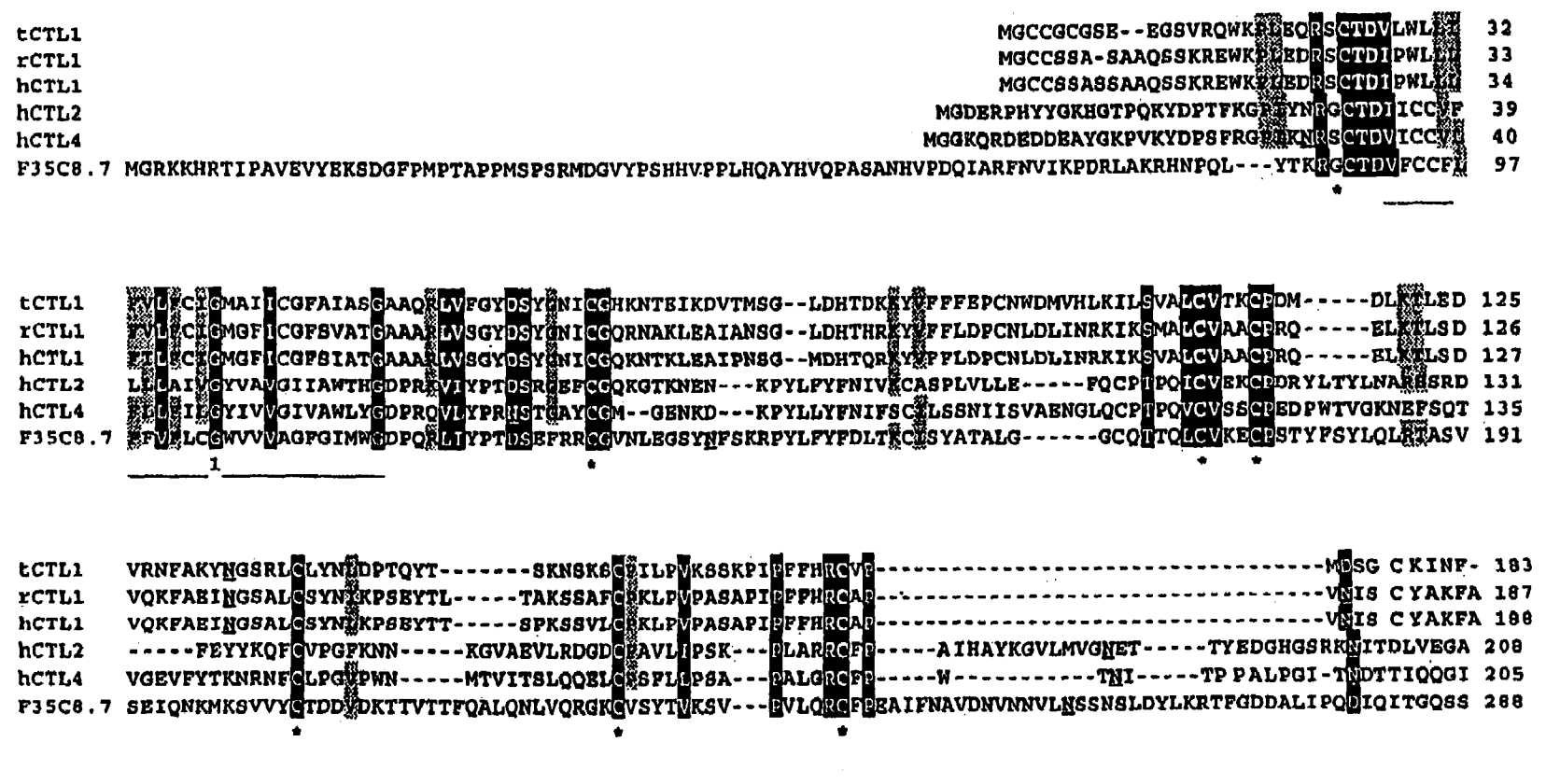
Figure 2B:
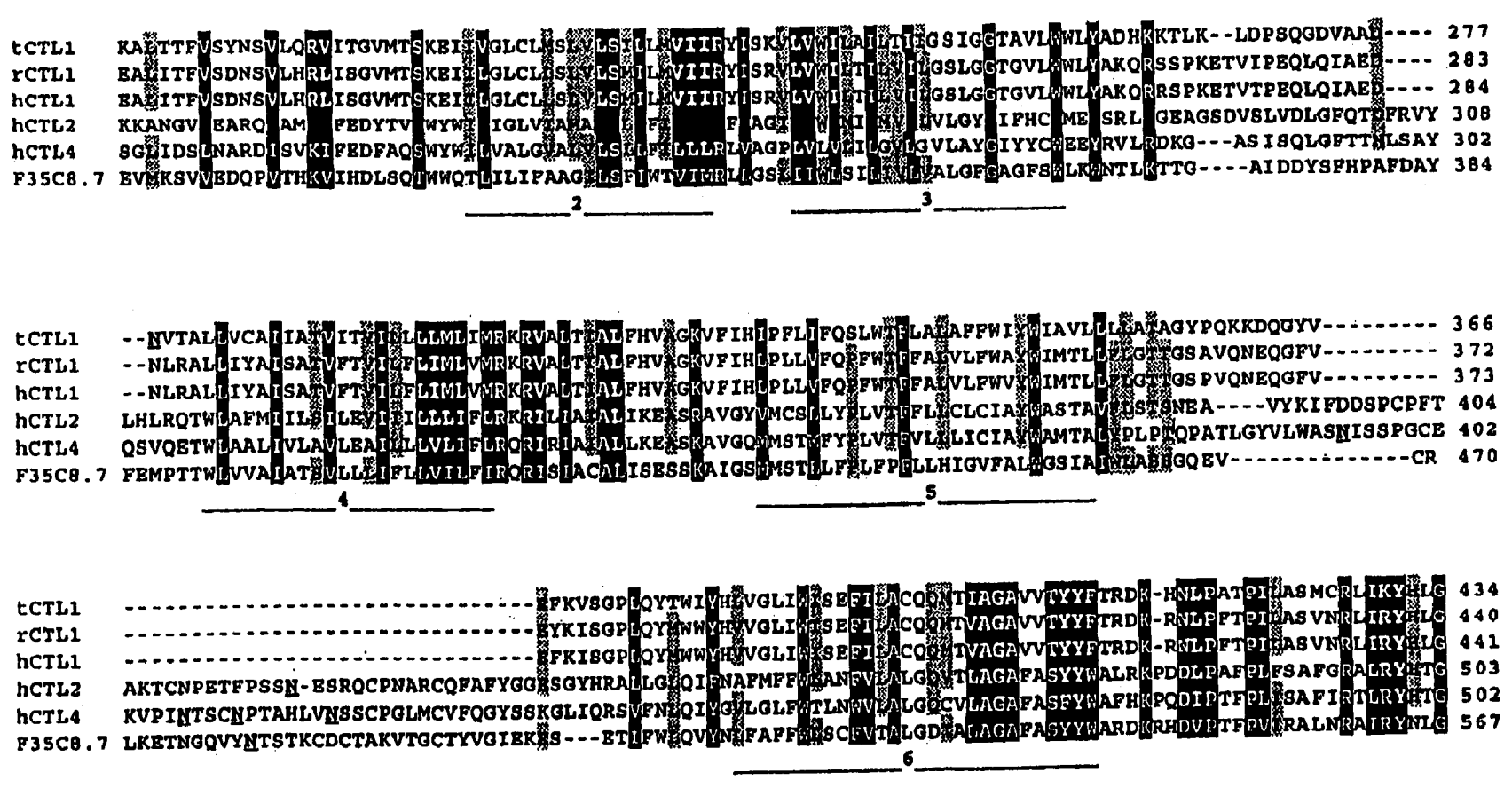
Figure 2C:
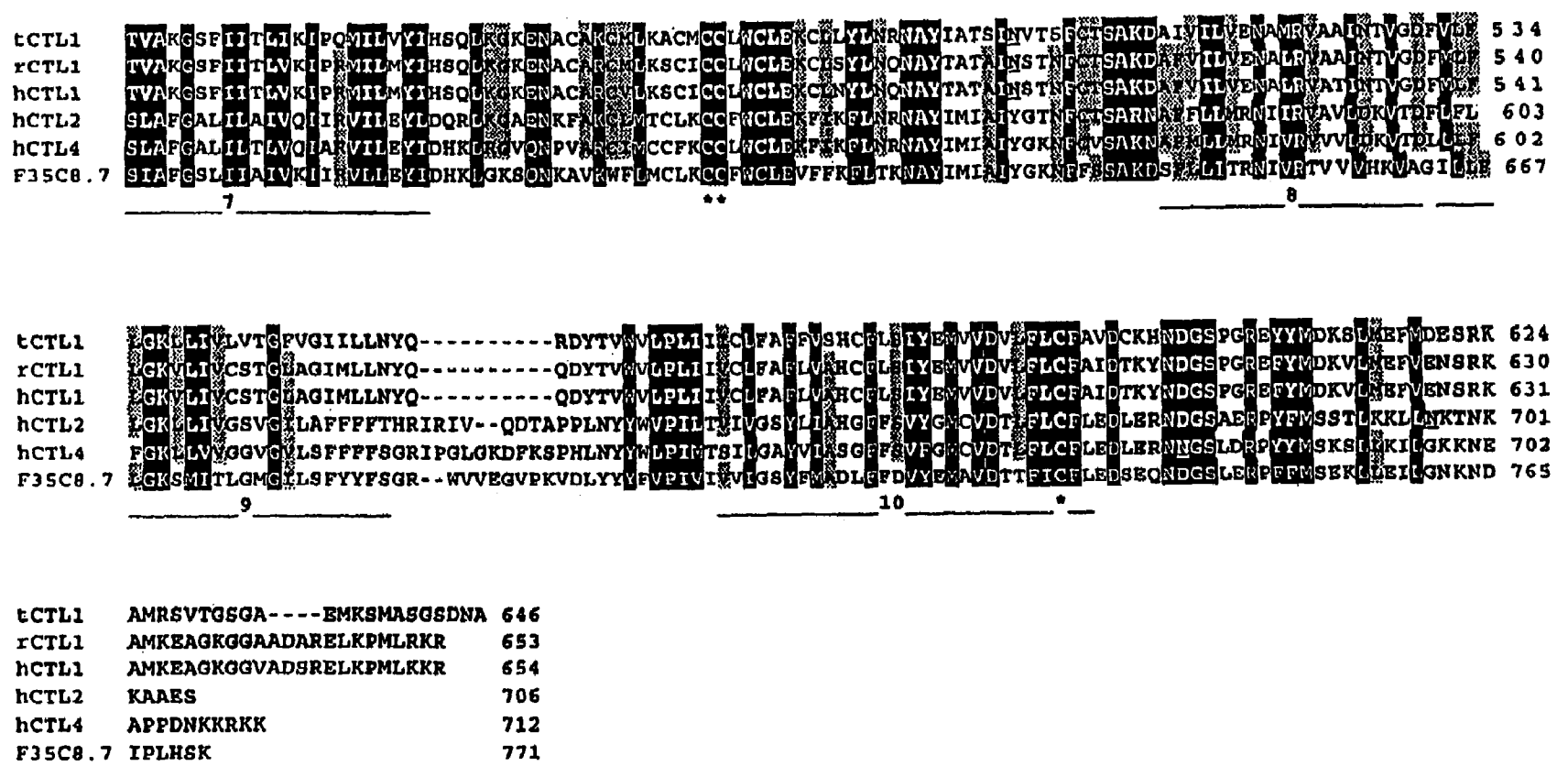

FIG. 2: Alignments of the CTL protein sequences and model for their membrane topology.

(A-C) Alignment of amino acid sequences of CTL1 obtained from torpedo (tCTL1), rats (rCTL1) and humans (hCTLI) with two homologous proteins, hCTL2 and hCTL4, and the single C. elegans homologous protein, F35C8.7. A black shading indicates 100% conservation and a light gray shading 80% conservation (Blosum 62). The 20 hydrophobic amino acid segments which can form the transmembrane domains (TMD) are indicated under the alignments and numbered. The potential N-glycosylation sites are underlined in each sequence. The conserved cysteines are marked with asterisks under the alignment.

(D) Structural model of CTLI.

(E) Dendrogram of CTL proteins and of the related proteins obtained using ClustalW. No homologs were found in prokaryotes. The asterisks indicate that only the partial protein sequences are used for the analysis.

Figure 3:
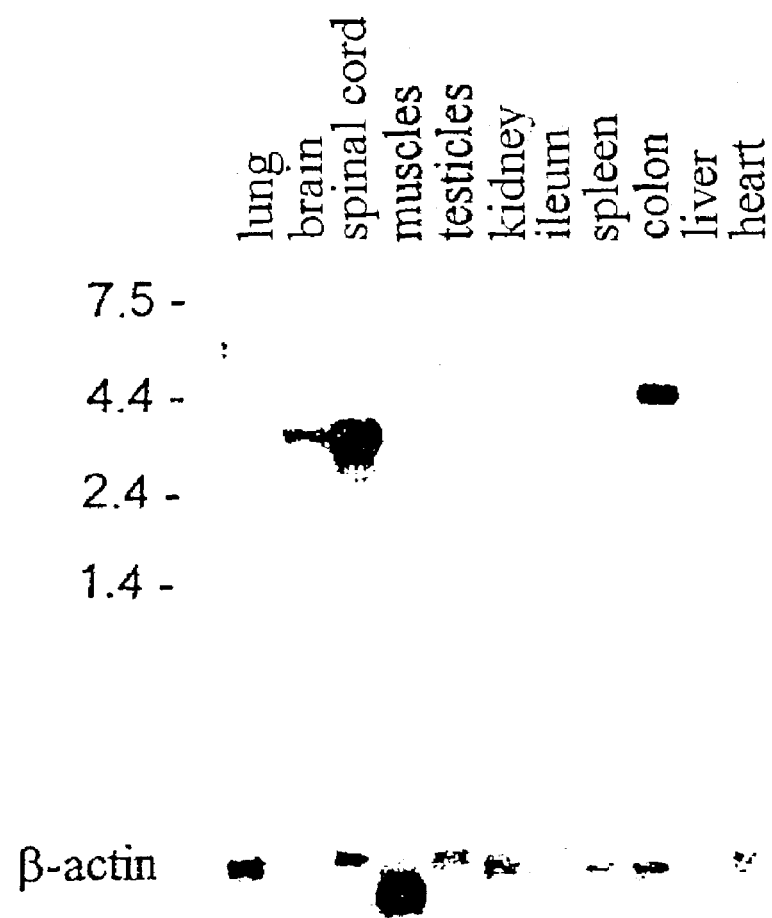

FIG. 3: Northern analysis of the rCTL1 mRNA in adult rat tissues.

Poly(A)+RNA (2 μg) obtained from specified tissues was hybridized with a probe for rCTL1 and exposed for 7 hours. The bottom part shows the hybridization with an (-actin probe.

FIGS. 4A-4F: Distribution of rCTL1 in adult rat tissues by ISH.

(A) This figure shows intense labeling with the antisense rCTL1 cRNA probe in the dispersed cells present at a higher density in the callous body (CC) than in the cells localized in the gray matter, and in the hippocampal neurons of Ammon's horn (CA1-CA3) and of the dentate gyrus (DG).

(B) A higher magnification of the labeled cells in the CC shows chains of cells, which suggests the labeling of oligodendrocytes (arrowheads).

(C) A frontal section of the cervical spinal cord shows a high density of labeled small cells present in the white matter as in the gray matter, as well as larger labeled cells observed in the ventral nuclei (arrowheads; VMnF, medioventral fissures).

(D) The cellular layer forming the mucous membrane of the colon (M) expresses high levels of products of transcription of rCTL1.

(E,F) Double ISH using the antisense probe for rCTL1 cRNA labeled with digoxigenin (E) and an antisense riboprobe for choline acetyltransferase labeled with fluorescein (F) results in the identification of large cells expressing rCTL1 in the form of motor neurons (arrowheads). The cryosections hybridized with sense probes labeled with digoxigenin and labeled with fluorescein do not exhibit a significant signal.

Figure 5:
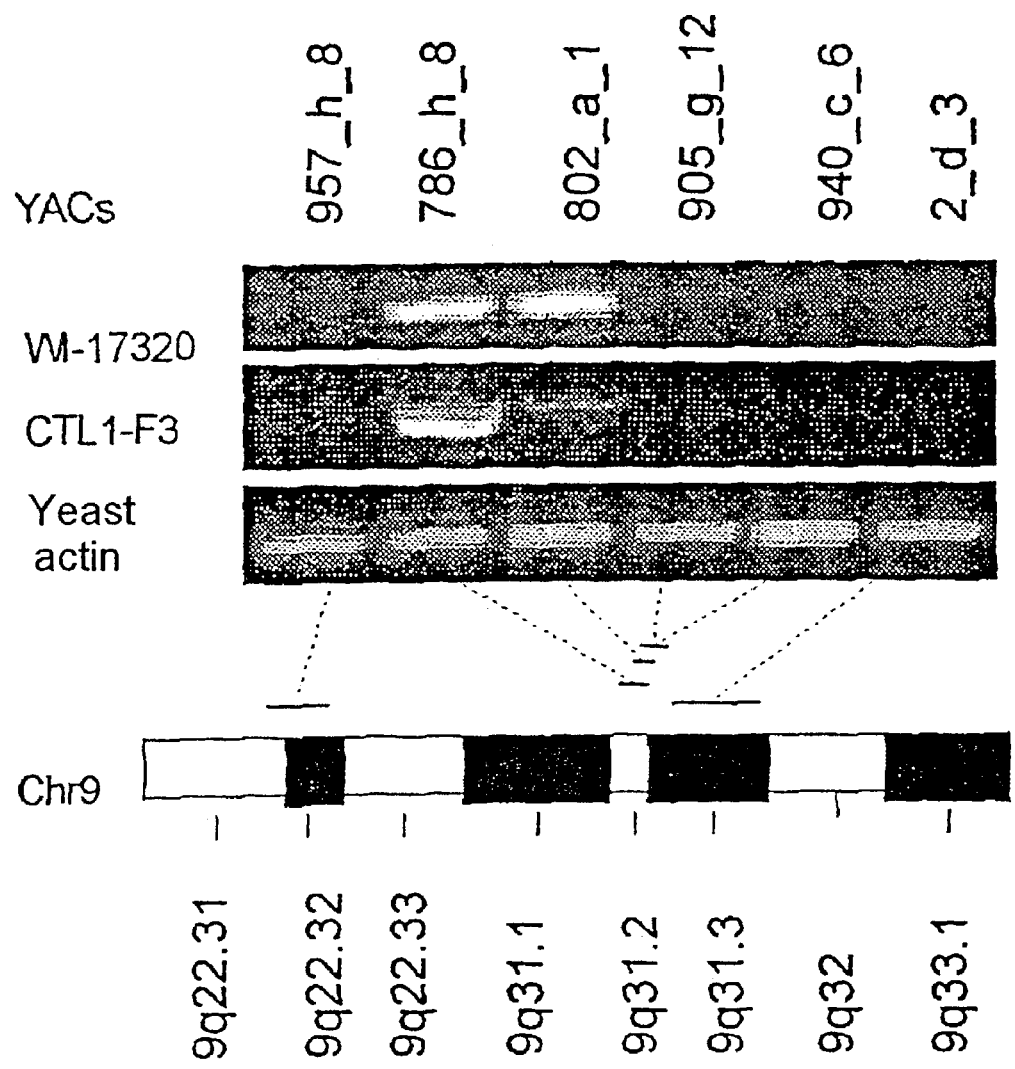

FIG. 5: Co-localization of WI-17320 and hCTL-F3 at YACs whose map is established in 9q31.2.

Among the 6 YACs tested, only the YACs 786-h-8 and 802-a-1 are found positive for the marker WI-17320 by PCR; the same YACs are also positive for a marker, CTLI-F3, for the coding region in 5' of hCTL1. It is also known that these two YACs carry the genetic marker D9S299. Yeast actin was used as positive control. The localization of the YACs on chromosome 9 (dotted lines leading to the bars) is based on the GDB map representation.

Figure 6:
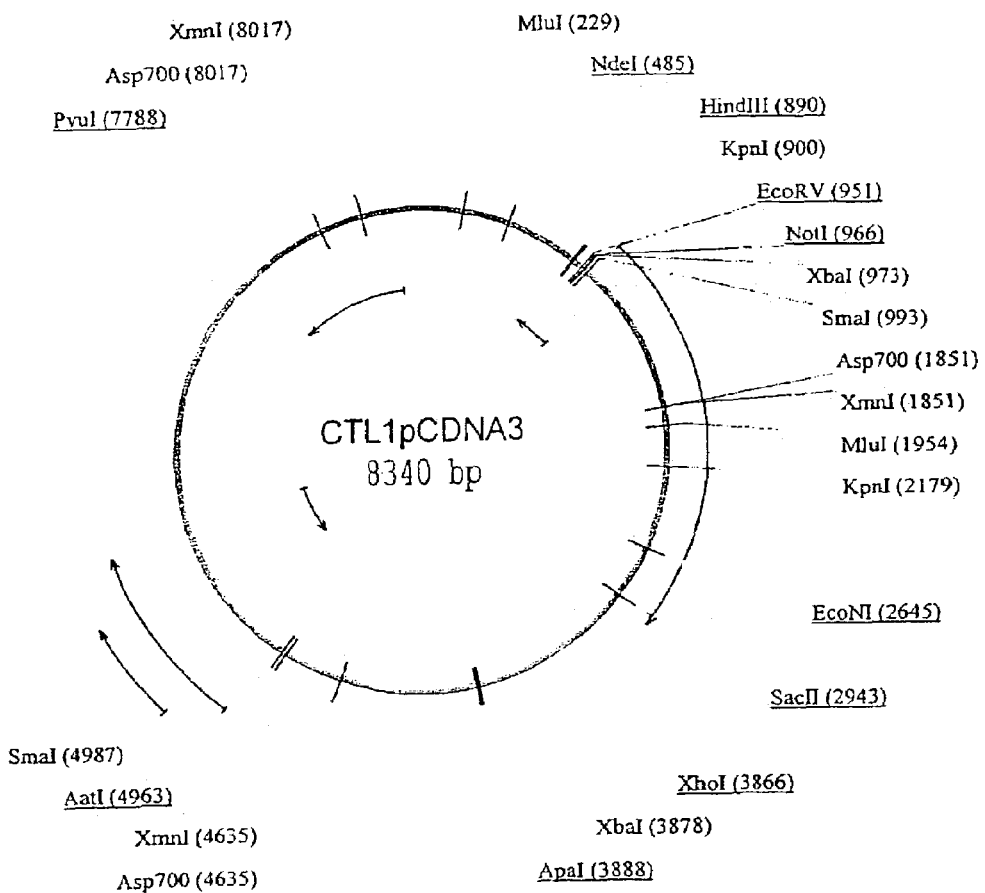

FIG. 6: Plasmid used for the transformation experiments. This plasmid was constructed from the mammalian expression vector pcDNA3.

Figure 7:
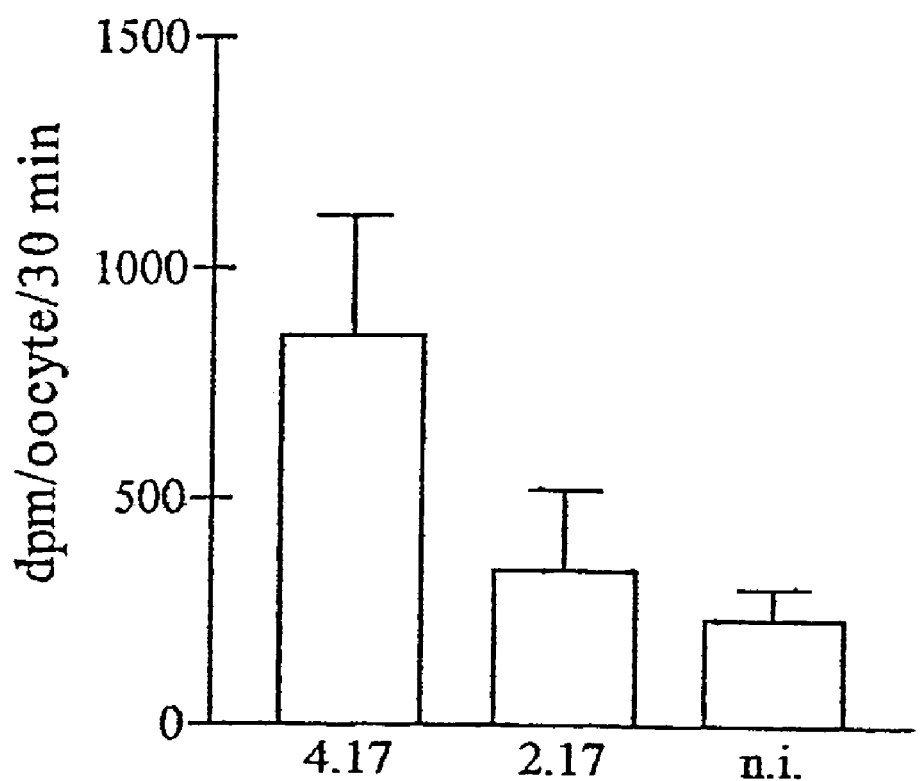

FIG. 7: Absorption of choline sensitive to HC-3. The clone 4.17 (tCTL1) was transcribed and injected into Xenopus oocytes in order to test the absorption of choline under physiological conditions. It should be noted that the high level of absorption of endogeneous choline makes the observation of the modifications of induced absorption difficult. However, the expression of tCTL1 causes an increase by a factor 3 in the absorption of choline sensitive to HC-3 in the presence of 88 mM NaCl.

Figure 8A:
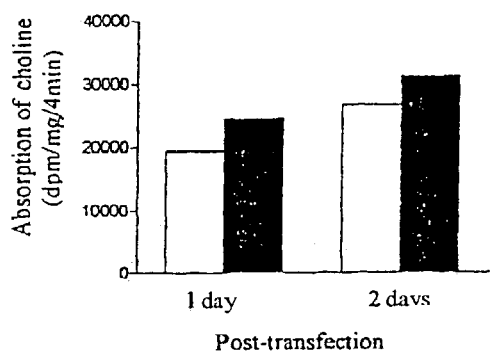
Figure 8B:
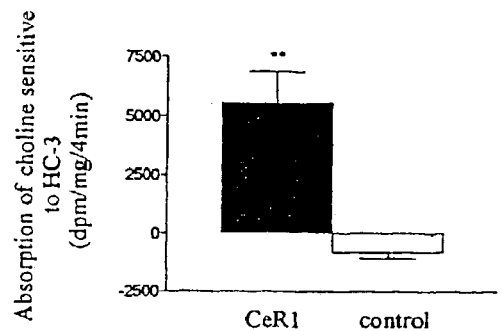
Figure 8C:
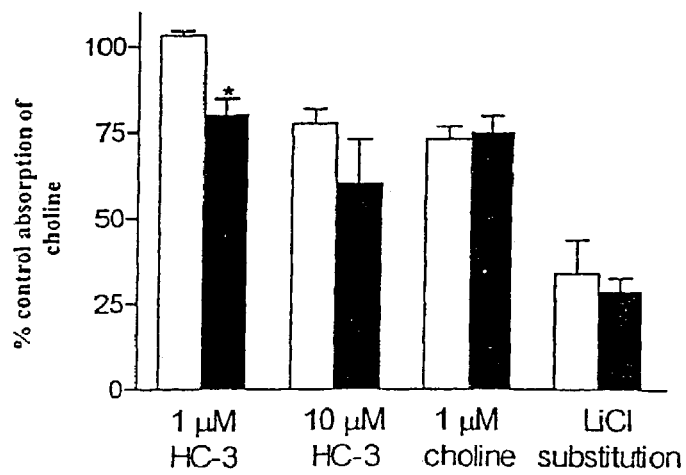

FIGS. 8A-8C: Transient transfection of glioma cell C6 with the vector CTL1pcDNA3 described in FIG. 6.

48 hours after transfection, only a marginal increase in total absorption of choline was observed compared with the cells transfected with an empty plasmid (negative control). However, only the C6—CTL1pcDNA3 cells show inhibition of total absorption of choline with 1(m of hemicholinium-3. Consequently, CTL1 is involved in the sensitivity to hemicholinium-3.

Figure 9A:
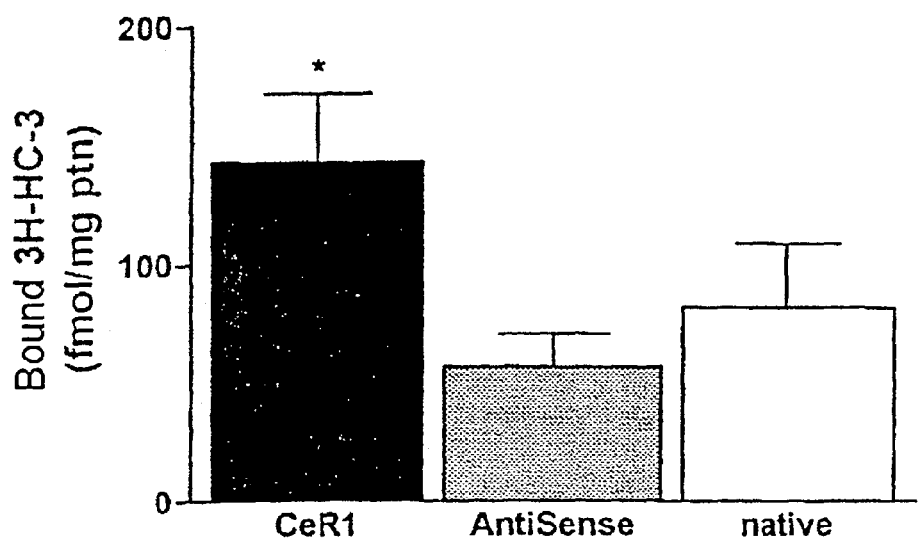
Figure 9B:
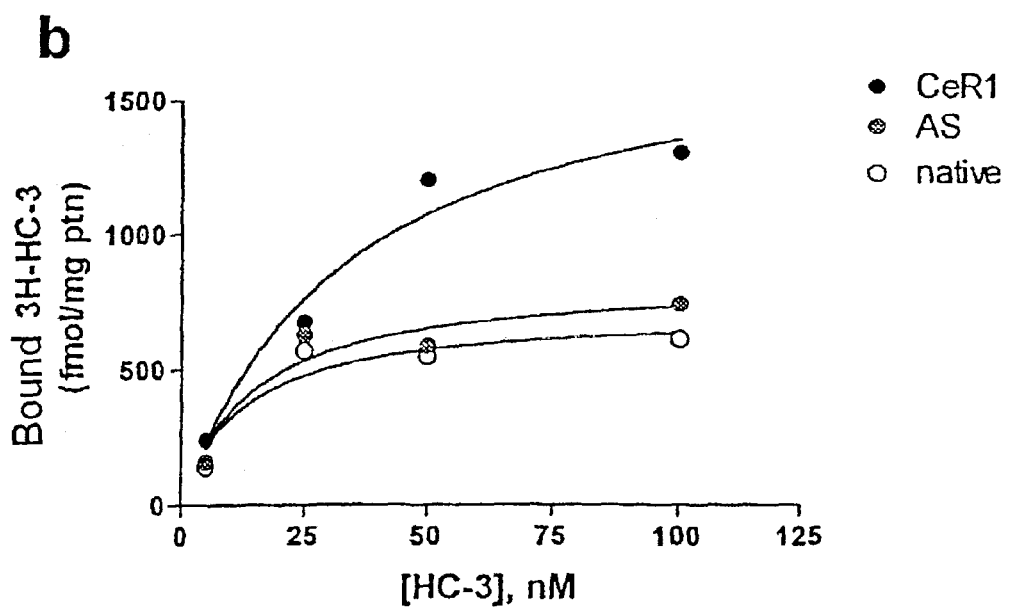

FIGS. 9A-9B: Stable transfection of glioma cells C6.

After selection with antibiotics and stabilization, the membranes of the cells expressing CLT1 (CeR1) retain twice as much hemicholinium-3 than the natural C6 cells or than the cells transfected with the antisense for CTL1. The expression of CTL1 is therefore associated with an increase in the number of choline transporter proteins.

FIG. 10: Alignments of the hCTL1a (SEQ ID NO: 9) and hCTL1b (SEQ ID NO: 1) protein sequences.

Alternative splicing of the transcripts of the CTL1 gene leads to the production of two proteins which differ in their C-terminal ends as indicated in the figure by characters in italics. These sequences could play different roles in the regulation, targeting or interactions of these proteins.

Figure 11:
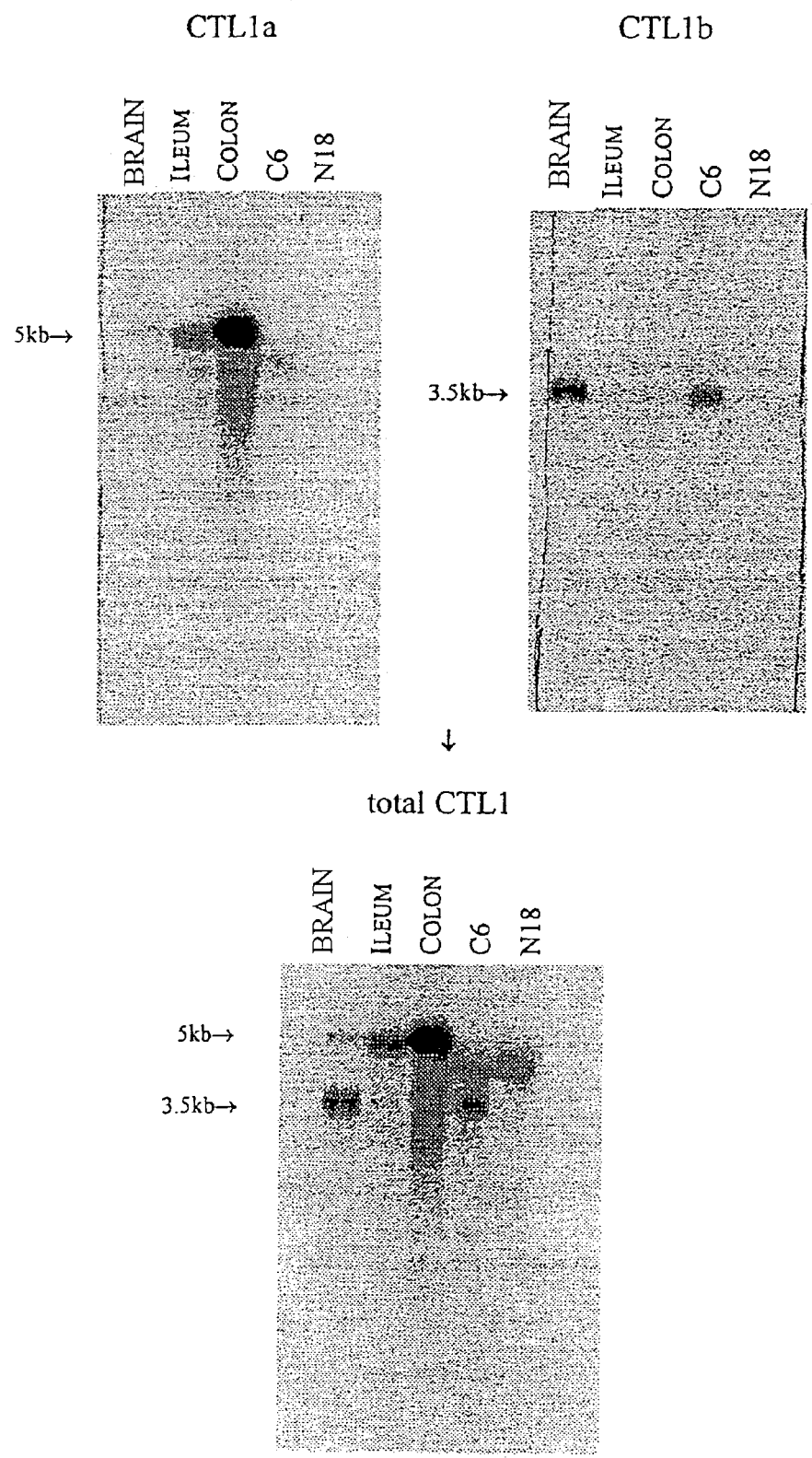

FIG. 11: Complementarity of expression of the mRNAs for rCTL1a and rCTL1b in adult rat tissues and cell lines by Northern blot analysis.

Probes specific for each mRNA make it possible to identify the tissues and the cells expressing either of the spliced forms and to characterize their size. The hybridization of the same blots with a probe corresponding to the common sequence shows that these two forms are the predominant forms of CTL1 in adult rat tissues. Among the cell lines examined, glioma C6 is distinguished by a high expression of CTL1b and by a transcript of intermediate size which is also detected in other lines such as the neuroblastoma N18. The quantities of poly(A)+RNA deposited were 2 µg for the brain and the colon, and 10 µg for the ileum, the C6 and N18 lines.

Figure 12:
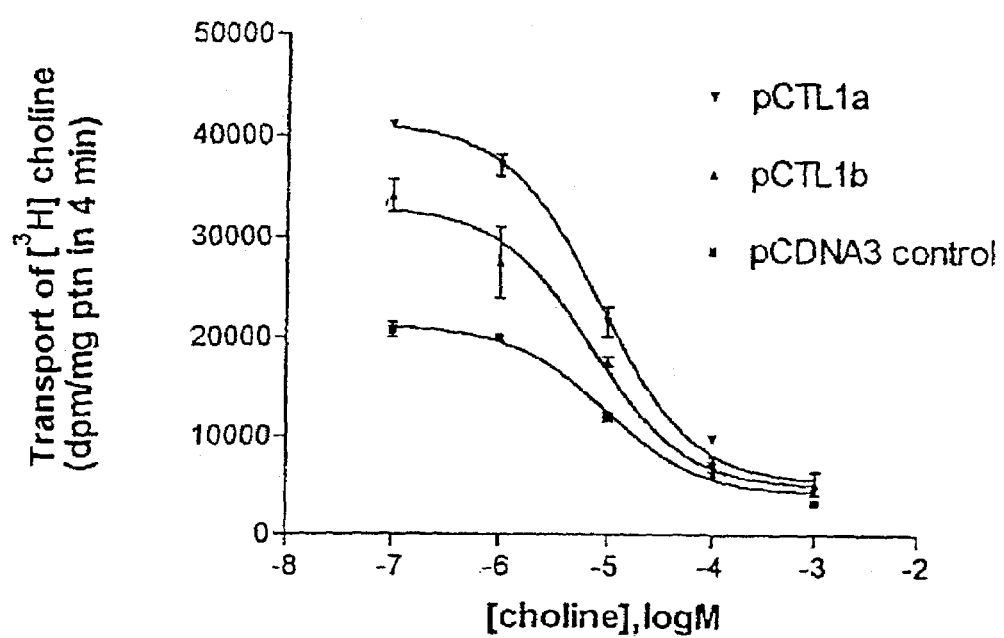

FIG. 12: Transport of choline by the N18 cells after transient transfection with the vectors rCTL1a/pcDNA3, rCTL1b/pcDNA3 and pcDNA3.

24 hours after transfection, a higher choline capture by the cells transfected with the recombinant plasmids is observed than by the cells transfected with the empty plasmid. In the three cases, the capture of tritiated choline is inhibited by about 50% in the presence of 10 µM of cold choline or of 10 µM of hemicholinium-3 (result not shown).

EXAMPLES 1

Complementation of the Choline Transport Mutation in Yeast

Materials and Methods

The yeast strain (ctr ise URA3( ) used in the context of the invention was obtained by growing D308-14D (ctr ise leu his4) (SEQ ID NO: 14)(6), with a URA3 strain ((9). This strain does not grow in a medium low in uracil, or in a high content of myoinositol, unless an external source of choline and a mechanism for choline absorption are both available. Poly(A)+ RNA was prepared from frozen electric lobes of torpedo marmorata. The corresponding cDNAs were inserted into the BstXI site of the plasmid pFL61 (9) using the Amersham cDNA cloning kit The yeast was transformed using the LiAc/SS-DNA (PEG) method (10). The transformed yeast was cultured on a solid medium under selective growth conditions (no uracil, 20 µg/ml of choline, 20 µg/ml of myoinositol) the reverse mutants were eliminated as being capable of growth in the absence of choline. The plasmids were isolated from colonies having a strong choline-dependent growth phenotype, and they were used to transform aliquot fractions of mutant yeast in order to eliminate the ctr reverse mutants and the yeast suppressor mutations. 5 clones were selected, and the absorption of choline was tested.

Absorption of Choline Per Recombinant Yeasts:

Aliquot fractions of mutant yeast were transformed with individual isolated plasmids and, after amplification, the absorption of choline was determined in a medium free of nitrogen (11) at 30° C. for 30 minutes with 25 mM [3H] choline (0.1 µCi, 2.8 TBq/mmol, Amersham), and then the medium is filtered and washed. The blanks were estimated by adding 1 mM nonlabeled choline, and subtracting. The culture density was normalized by measuring the OD600.

Results

Complementation for the choline-dependent growth under conditions selective for the mutant yeast (ctr ise URA 30 transformed with a torpedo electric lobe yeast expression library in pFL61 led to the isolation of a single clone called 4.17, associated with an increase in the saturable [3H] choline absorption by the mutant yeast (FIG. 1A). It is known that the high-affinity choline absorption by the cholinergic nerve endings depends on sodium and is inhibited by low concentrations of hemicolinium-3 (HC3)(1.17); the saturable [3H]choline absorption by the yeast transformed in 4.17 is inhibited by HC-3 at a low concentration (1 µM), but the addition of 100 mM NaCl to the medium reduces the signal, may be because of the resulting hyperosmolarity for the yeast (FIG. 1B). The HC-3 inhibiting effects and the hyperosmotic addition of NaCl are not additive, which suggests that the two treatments inhibit the same component of choline absorption.

Consequently, clone 4.17 of the electric lobe acts as a suppressor of yeast choline transport mutation, and the absorption of the choline of the yeast expressing 4.17 is sensitive to HC-3 but not dependent on sodium, and therefore only partially resembles the neuronal choline transporter. Thus, the sequencing of the cDNA corresponding to clone 4.17 indicates that it encodes a truncated transmembrane protein of 175 aa comprising 3 TMDs before the stop codon. It is not impossible that the truncated vertebrate transmembrane protein is more easily directed toward the yeast plasma membrane (18).

EXAMPLE 2

Cloning and Analysis of Orthologous and Homologous Sequences of CTL1

Materials and Methods

Full-length cDNAs, suppressors of yeast choline transport mutation, tCTL1 and its ortholog in rats, rCTL1, were isolated from (ZAP II (Stratagene) libraries constructed from the electric lobe of T. marmorata and from rat brain, respectively. The complete sequence of a tCTL1 clone of 4.4 kb and of an rCTL1 clone of 2.9 kb were obtained using both Sequenase T7 (Amersham) and an external sequencing service (ESGS-Cybergene, Evry). The predicted transmembrane domains (TMD) of the CTL proteins were attributed on the basis of Kyte and Doolittle hydropathy graphs. The homologous expressed sequence tags (EST) were assembled using the BLAST program. The sequences were completed for the coding region of the human ortholog hCTL1 (Unigene Acc.: Hs. 179902), and its homolog hCTL2 (Unigene Acc: Hs. 167515 and Hs. 105509) by sequencing PCR products obtained using the DNA obtained from the Ewing's sarcoma cell line, ICB 112 (12). Other full-length coding sequences were available as conceptual translations of genomic sequence: murine NG22 (gbAcc: AAC84166) and human NG22 (gbAcc: AAD21813) are renamed here, respectively, mCTL4 and hCTL4; C. elegans F35C8.7; yeast YOR 161c; A. thaliana F20M13.200. The alignment of chosen sequences was carried out using gcg:PILEUP. EST analysis indicates homologs of CTL1 in Drosophila (gbAcc: AA697340), Dictyostelium (gbAcc: C24622), and another human homolog which the inventors call hCTL3 (gbAcc: Aa329432) and its murine equivalent, mCTL3 (gbAcc: W64177). The agglutination relations between these proteins are presented in the form of a dendrogram drawn using ClustalW.

Figure 2D:
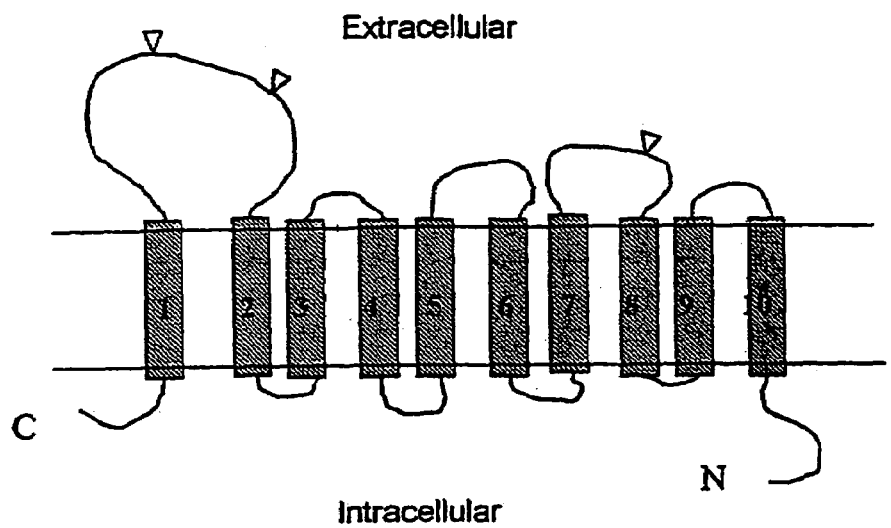
Figure 2E:
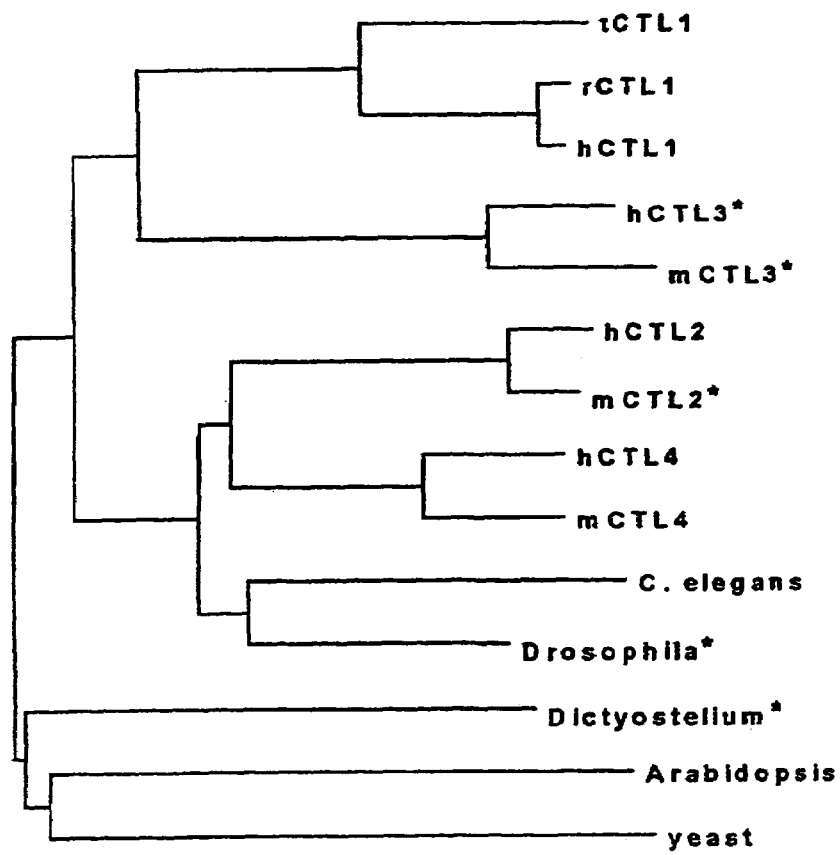

Results:

The protein sequences for the cloned genes (tCTLI and rCTLI) and their human ortholog (hCTL1, 96% identity with the rat) are presented in FIGS. 2A-C. The members 15 of a family of several related proteins were in addition found in humans and mice: hCLT4 (43% homology with hCTLI) and mCTL4 from conceptual translations of human and murine genomic sequences (see Materials and Methods above); and hCTL2 (43% homology with hCTLI and 67% homology with hCTL4), for which the complete coding sequence was obtained. All these sequences are homologous to a 20 single gene found in the genome of C. elegans, F35C8.7 (FIGS. 2A-C). Domain analyses with the databases BLOCKS or PROSITE and the search for motif are not consensual, but the transporters are frequently cited in the alignments with the transmembrane domains TMD 2 and 3 (FIG. 2D). All these proteins have several transmembrane domains and it can be reasonably thought that they cross the membrane ten times 25 (FIG. 2D). The other major characteristics of the proteins of this family are the following: a first large and variable extracellular loop between TMDs 1 and 2, which is potentially glycosylated, with 6 conserved cysteines; a third small variable extracellular loop between TMDs 5 and 6, which is glycosylated in some proteins, a highly conserved region which covers the last 4 TMDs and includes the fourth 5 extracellular loop which contains three conserved cysteins and is only potentially glycosylated in the orthologs of CTLI; and the variable intracellular N- and C-terminal ends. Advantageously, the conserved region includes the suppressor, 4.17, whose first ATG corresponds to M471 of tCTLI. The proteins lack a clear signal peptide and they are expected to be targeted onto the plasma membrane.

The relationships between these sequences and other partial sequences for another protein, CTL3, in mice and humans, and with the more distant homology in other eukaryotes, including conceptual translations from plant genomes, are presented in FIG. 2E. In humans, the members of this family, hCTL2 and hCTL4, more closely 15 resemble the single C. elegans gene (51-52% homology) than hCTLi and hCTL3 (38% homology). The two plant proteins show only 25% homology with the C. elegans gene. Taken together, the information on the structure and the relationships of these sequences shows that they are indeed a new family of CTL protein (abbreviation of C. elegans transporter-like proteins).

EXAMPLE 4

Analysis of the Expression of rCTL1 in Tissues

Materials and Methods:

a) Northern Blotting.

The poly(A)+RNA (2 µg) extracted from various rat tissues was analyzed by Northern blotting using a BamHI/EcoRI fragment in 5' of rCTL1 labeled with [32P]dCTP, and washed under stringent conditions. It was exposed for 7 and then 40 hours (not represented), and hybridized with, an (-actin probe as control.

b) In situ Hybridization

The ISH experiments were carried out as described in (14), modification of the Schaeren-Wiemers and Gerlin-Moser protocol (13). A 1.6 kb PstI restriction fragment derived from rCTL1 was subcloned into pGEM-4Z and used to synthesize antisense and sense riboprobes labeled with digoxigenin. The double ISH protocol (15) was used using a fluorescein-labeled choline acetyltransferase riboprobe encoding a fragment corresponding to nucleotides 1-2332 (16). The sense riboprobe for rCTL1 did not give a specific signal, whereas the antisense cRNA probe resulted in reaction products which were observed in a cytoplasmic ring around the cellular nucleus.

Figure 4A:
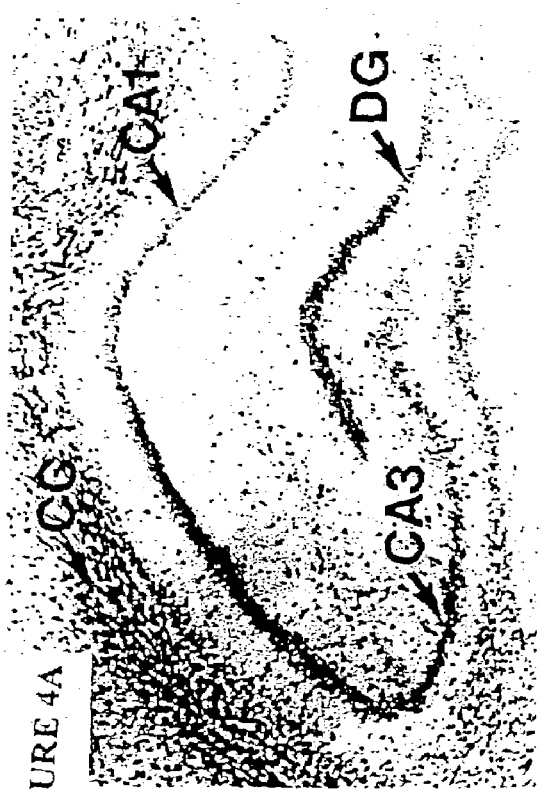
Figure 4B:
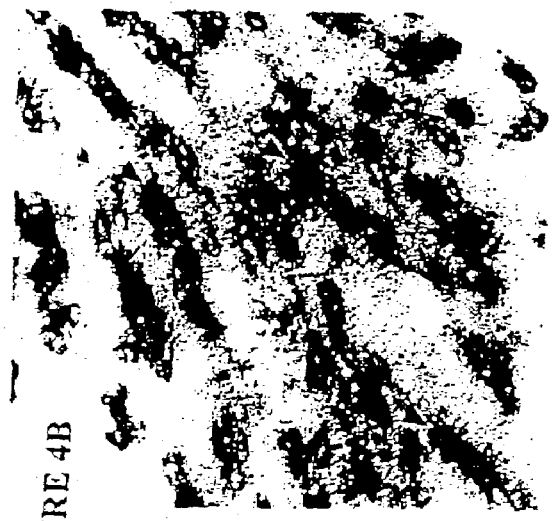
Figure 4C:
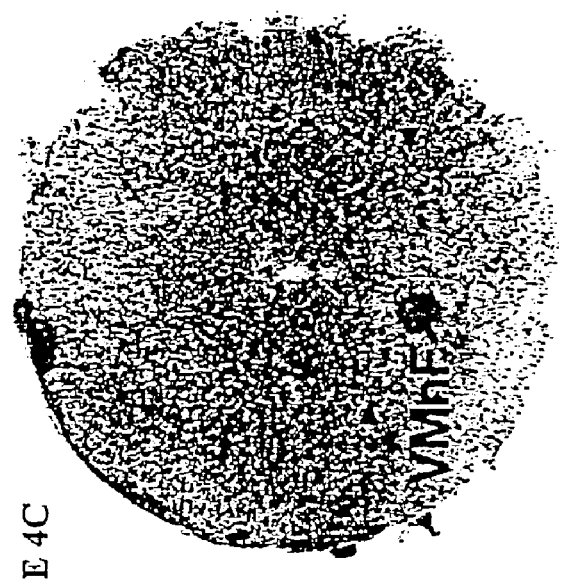
Figure 4D:
Figure 4F:
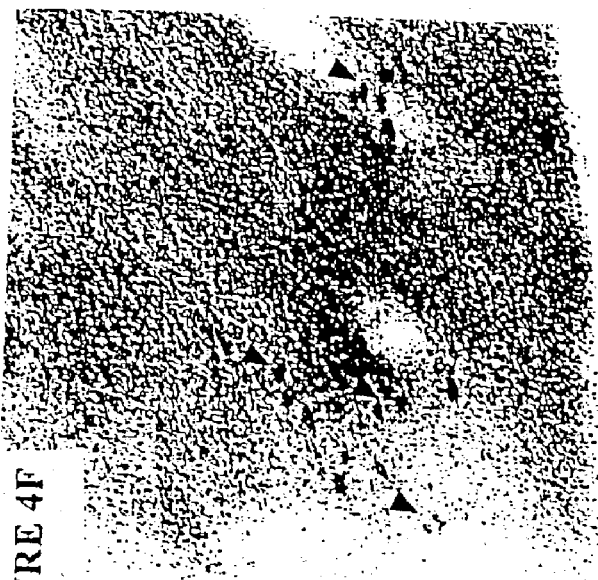
Figure 4E:
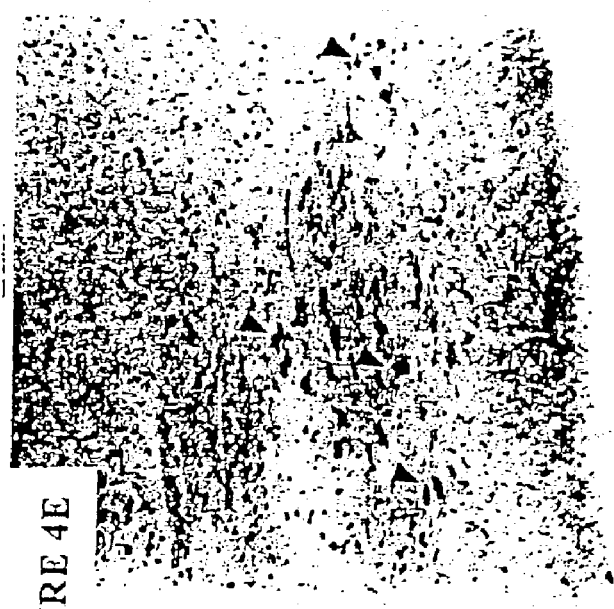

Results:

Northern analysis of the distribution of rat mRNA with an rCTL1 probe exhibits a particularly striking signal of 3.5 kb in the spinal cord and to a lesser degree in the brain, whereas a larger form of 5 kb is present in the colon, in the lung and the spinal cord (FIG. 3). The 5 kb form appears fairly frequent and of low intensity (40 hours of exposure, not represented), whereas no signal is detected at 3.5 kb for the liver, the spleen or the ileum under the same conditions. A more careful examination of the tissues exhibiting high expression by ISH shows that several types of cell express rCTL1 (FIG. 4). In the spinal cord, the highest expression is observed in the large cells of the ventral horn, which are identified as motor neurons by double ISH experiments using, in addition, an antisense riboprobe for cRNA for choline acetyl-transferase (FIG. 4E, F). The results also show a fairly high expression of products of transcription of rCTL1 in neurons assumed to be motors in the facial nucleus, which suggests an important role in these cholinergic neurons. However, other neurons expressing the mRNA for choline acetyltransferase, such as those found in the septal zones or the basal nucleus, do not exhibit high levels of mRNA for rCTL1. Furthermore, rCTL1 is not a specific marker for the cholinergic neurons, even in the spinal cord, because a high density of rCTL1 was detected in cells dispersed in the gray matter as in the white matter (FIG. 4C). In the gray matter, the small cells labeled could correspond to oligodendrocytes and to interneurons. Thus, in the brain, the expression of the mRNA for rCTL1 is particularly high in the bundles of myelinized fibers. The results also show a high density of intensely labeled cells in the cerebellar white matter, the brainstem, the callous body, the hippocampal fimbriae and the lateral olfactory peduncle. In these zones, the labeled cells appear in the form of a short chainb 4B) as has been shown for the oligodendrocytes (19). The double ISH experiments using a riboprobe specific for the myelin basic protein, a marker for oligodendrocytes (19) and rCTL1 which were carried out on the white matter of the cerebellum indicate that rCTL1 is indeed expressed in the oligodendrocytes. rCTL1 is also expressed at a lower level in neurons dispersed throughout the brain, as for example in the hippocampal formation where products of transcription of rCTL1 are observed in the pyramidal cells of Ammon's horn and the granular cells of the dentate gyrus (FIG. A4), and in cells dispersed throughout the hippocampal formation. Thus, rCTL1 appears to be expressed by both the neurons and the oligodendrocytes of the central nervous system (CNS).

The expression of rCTL1 also occurs outside the CNS, in particular in the colon, where the largest product of transcription is frequent. In the colon, high levels of expression were observed in the cellular layer of the mucous membrane of the invaginations as in that of the lumen (FIG. 4D).

EXAMPLE 5

Positioning of hCTL1 on Chromosome 9 Using Yeast Artificial Chromosomes (YACs)

Materials and Methods

A sequence rigged site (STS: WI-17320) was linked to an EST corresponding to the coding region in 3' of hCTL1. YACs in the indicated region, 9q22/31, are obtained from the Center for the Study of Human Polymorphism (France). Yeast harboring YACs was used for the PCR analysis. The PCR primers for W1-17320 are as given (gbAcc: G24229) and for yeast actin (gbAcc: X61502) are forward and backward primers: CAAAATTGGCTAGAGAAACAACCG (SEQ ID NO: 5) and backward primers: AAAGA ACAATG-GCCTTATACAGG (SEQ ID NO: 6). The primers used to locate the coding region of the hCTL1 gene are forward primers: CATGT GGTGGTACCATGTGGTGGG (SEQ ID No. 7) and backward primers: CGAATAAGGCGATTT ACTGATGCC (SEQ ID NO: 8). The PCR product using the latter primers, CTL1-F3, is longer than predicted by the cDNA, that is 762 bases instead of 161 because it possesses an intron.

Results:

Analysis of the human ESTs also indicates that the sequences associated with hCTL1 include an STS, WI-17320, which was localized in 9q22/31. No YAC is known which carries this marker, such that 6 YACs, whose position in this locus has been established, were chosen in order to carry out tests, and it was found, by PCR analysis, that two of them, 786-H-8 and 802-A-1, are positive for WI-17320. Only these two YACs are also positive for a marker, CTL2-F3, defined for the coding region in 5' of hCTL1 (FIG. 5). The two YACs also carry the genetic marker D9S299, which indicates a more precise localization of hCTL1 in 9q31.2. D9S299 is just proximal relative to the familial dysautonomia mutation locus (MIM 223900) (20), and inside the larger locus given for Tangier disease (MIM 205400) (21).

Information is also available on the chromosomal localization of hCTL4 and hCTL2; human NG22 (hCTL4) was sequenced as part of the major histocompatibility complex III in 6p21.3, and the hCTL2 sequence assembled includes two STSs whose map was independently established in 19p13.1. Consequently, CTL resembles numerous human genes with duplication between chromosomes 1, 6, 9 and 19(22-24).

EXAMPLE 6

Two Forms of CTL1 Derived from Alternative Splicing

We demonstrated an alternative splicing on the gene encoding the CTL1 protein in humans and in rats. This splicing leads to two proteins hCTL1a (SEQ ID NO: 9) and hCTL1b (SEQ ID NO: 3), which differ only in their C-terminal end. The sequences preceding the stop codon are respectively MLKKR (residues 650-654 of SEQ ID NO: 3) for hCTL1b and MASGASSA (residues 650-657 of SEQ ID NO: 9) for hCTL1a (FIG. 10). These two forms have a different tissue distribution. In rats, CTL1b is predominantly expressed in the brain, whereas CTL1a is predominantly expressed in the intestine (FIG. 11). On the cellular scale, in situ hybridization experiments using the probes rCTL1a and rCTL1b, respectively, on brain sections show that the two transcripts are present in the glial cells, but only rCTL1a is expressed in certain neuronal populations. The colocalization of rCTL1a and rCTL1b is found in a glial line, the glioma C6 (FIG. 11). After transfection into the N18 cell line only expressing a slight amount of endogenous CTL1 (FIG. 11), the plasmids containing the cDNAs encoding rCTL1a or rCTL1b both induce an increase in the capture of tritiated choline by the cells (FIG. 12).

These two proteins are endowed with choline transporting activity, and their differential expression may open a way to the development of molecules with selective action.

REFERENCES

1. Yamamura, H. I. & Snyder, S. H. (1973) J. Neurochem. 21, 1355-1374.
2. Kuhar, M. J. & Murrin, L. C. (1978) J. Neurochem. 30, 15-21.
3. Jope, R. S. (1979) Brain Res. 180, 313-344.
4. Knipper, M., Kahle, C. & Breer, H. (1991) Biochim. Biophys. Acta 1065, 107-113.
5. Rylett, R. J., Walters, S. A. & Davis, W. (1996) Brain Res. Mol. Brain Res. 35, 354-358.
6. Nikawa, J., Tsukagoshi, Y. & Yamashita, S. (1986) J. Bacteriol. 166, 328-330.
7. Sentenac, H., Bonneaud, N., Minet, M., Lacroute, F., Salmon, J. M., Gaymard, F. & Grignon, C. (1992) Science 256, 663-665.
8. Nikawa, J., Hosaka, K., Tsukagoshi, Y. & Yamashita, S. (1990) J. Biol. Chem. 265, 15996-16003.
9. Minet, M., Dufour, M. E. & Lacroute, F. (1992) Plant J. 2, 417-422.
10. Gietz, R. D., Schiestl, R. H., Willems, A. R. & Woods, R. A. (1995) Yeast. 11, 355-360.
11. Hosaka, K. & Yamashita, S. (1980) J. Bacteriol. 143, 176-181.
12. O'Regan S., Diebler, M.-F., Meunier, F.-M. & Vyas S. (1995) J. Neurochem. 64, 69-76.
13. Schaeren-Wiemers, N. & Gerfin-Moser, A. (1993) Histochemistry 100, 431-440.
14. Traiffort, E., Charytoniuk, D. A., Watroba, L., Faure, H., Sales, N. & Ruat, M. (in press) Eur. J. Neuroscl.
15. Arce, V., Pollock, R. A., Philippe, J. M., Pennica, D., Henderson, C. E. & deLapeyriere, O. (1998) J. Neurosci. 18, 1440-1448.
16. Brice, A., Berrard, S., Raynaud, B., Ansieau, S., Coppola, T., Weber, M. J. & Mallet, J. (1989) J. Neurosci. Res. 23, 266-273.
17. Haga, T. & Noda, H. (1973) Biochim. Biophys. Acta 291, 564-575.
18. Hogue, D. L., Ellison, M. J., Young, J. D. & Cass, C. E. (1996) J. Biol. Chem. 271, 9801-9808.
19. Shiota, C., Miura, M. & Mikoshiba, K. (1989) Brain Res. Dev. Brain Res. 45, 83-94.
20. Blumenfeld, A., Slaugenhaupt, S. A., Axelrod, F. B., Lucente, D. E., Maayan, C., Liebert, C. B., Ozelius, L. J., Trofatter, J. A., Haines, J. L. & Breakefield, X. O. (1993) Nat. Genet. 4, 160-164.
21. Rust, S., Walter, M., Funke, H., von Eckardstein, A., Cullen, P., Kroes, H. Y., Hordijk, R., Geisel, J., Kastelein, J., Molhuizen, H. O., Schreiner, M., Mischke, A., Hahmann, H. W. & Assmann, G. (1998) Nat. Genet. 20, 96-98.
22. Katsanis, N., Fitzgibbon, J. & Fisher, E. C. (1996) Genomics 35, 101-108.
23. Sugaya, K., Sasanuma, S., Nohata, J., Kimura, T., Fukagawa, T., Nakamura, Y., Ando, A., Inoko, H., Ikemura, T. & Mita, K. (1997) Gene 189, 235-244.
24. Hughes, A. L. (1998) Mol. Biol. Evol. 15, 854-870.
25. Blusztajn, J. K. & Wurtman, R. J. (1983) Science 221, 614-620.
26. Wurtman, R. J. (1992) Trends. Neurosci. 15, 117-122.
27. Mittag, T. W., Mindel, J. S. & Green, J. P. (1974) Ann. N.Y. Acad. Sci. 228, 301-306.
28. Pearson, J. & Pytel, B. A. (1978) J. Neurol. Sci. 39, 47-59.
29. Blumenfeld, A., Slaugenhaupt, S. A., Liebert, C. B., Temper, V., Maayan, C., Gill, S., Lucente, D. E., Idelson, M., MacCormack, K., Monahan, M. A., Mull, J., Leyne, M., Mendillo, M., Schiripo, T., Mishori, E., Breakefield, X., Axelrod, F. B. & Gusella, J. F. (1999) Am. J. Hum. Genet. 64, 1110-1118.
30. Engel, W. K., Dorman, J. D., Levy, R. I. & Fredrickson, D. S. (1967) Arch. Neurol. 17, 1-9.
31. LeBlanc, M. J., Gavino V., Perea, A., Yousef, I. M., Levy, E. & Tuchweber, B. (1998) Biochim. Biophys. Acta 1393, 223-234.

The invention claimed is:

1. A purified or isolated nucleic acid comprising a nucleic acid sequence selected from the group consisting of:
   a) the sequence SEQ ID NO: 1;
   b) the complementary sequence of SEQ ID NO: 1; and
   c) the RNA sequence corresponding to SEQ ID NO: 1.

2. An isolated nucleic acid encoding a polypeptide selected from the group consisting of:
   SEQ ID NO: 3: and
   SEQ ID NO: 9.

3. A vector comprising a nucleic acid sequence selected from the group consisting of:
   a) the sequence SEQ ID NO: 1; and
   b) the complementary sequence or the RNA sequence corresponding to SEQ ID NO: 1.

4. A vector comprising a nucleic acid sequence encoding a polypeptide selected from the group consisting of:
   SEQ ID NO: 3; and
   SEQ ID NO: 9.

5. The vector of claim 3 or 4, wherein the sequence is fused with a promoter which is effective in eukaryotic or prokaryotic cells.

6. An isolated cell transformed with the vector of claim 3 or 4.

7. A method for the amplification and/or detection of a target nucleic acid in a sample, said target nucleic acid having a sequence selected from the group consisting of:
   a) the sequence SEQ ID NO: 1;
   b) the complementary sequence or the RNA sequence corresponding to a sequence as defined in a); and
   c) a sequence capable of hybridizing to a sequence as defined in a) or b), the method comprising:
   hybridizing the sample with a primer and/or probe comprising at least 12 contiguous nucleotides comprising a sequence complementary to said target polynucleotide in the sample, and which probe specifically hybridizes to said target polynucleotide, under conditions whereby a hybridization complex is formed between said probe and said target nucleic acid.

8. A method for the amplification and/or detection of a target nucleic acid in a sample, said target nucleic acid encoding a polypeptide selected from the group consisting of:
   a) SEQ ID NO: 3; and
   b) SEQ ID NO: 9;
or a sequence capable of hybridizing to a nucleic acid sequence encoding a) or b) the method comprising:
   hybridizing the sample with a primer and/or probe comprising at least 12 contiguous nucleotides comprising a sequence complementary to said target polynucleotide in the sample, and which probe specifically hybridizes to said target polynucleotide, under conditions whereby a hybridization complex is formed between said probe and said target nucleic acid.

* * * * *

SEQUENCE LISTING

```
<160> NUMBER OF SEQ ID NOS: 14

<210> SEQ ID NO 1
<211> LENGTH: 2224
<212> TYPE: DNA
<213> ORGANISM: Homo sapiens

<400> SEQUENCE: 1
gctgcgcgca cgcgaccgca tccgggctcc ttcggccccg ccatgggctg ctgcagctcc      60
gcttcctccg ccgcgcagag ctccaaacga gaatggaagc cgctggagga ccgtagctgc     120
acagacatac catggctgct gctcttcatc ctcttctgca ttgggatggg atttatttgt     180
ggcttttcaa tagcaacagg tgcagcagca agactagtgt caggatacga cagctatgga     240
aatatccgtg ggcagaaaaa tacaaagttg gaagcaatac caaacagtgg catggaccac     300
acccagcgga agtatgtatt ctttttggat ccatgcaacc tggacttgat aaaccggaag     360
attaagtctg tagcactgtg tgtagcagcg tgtccaaggc aagaactgaa aactctgagt     420
gatgttcaga agtttgcaga gataaatggt tcagccctat gtagctacaa cctaaagcct     480
tctgaataca ctacatctcc aaaatcttct gttctctgcc ccaaactacc agttccagcg     540
```

-continued

| | |
|---|---|
| agtgcaccta ttccattctt ccatcgctgt gctcctgtga acatttcctg ctatgccaag | 600 |
| tttgcagagg ccctgatcac ctttgtcagt gacaatagtg tcttacacag gctgattagt | 660 |
| ggagtaatga ccagcaaaga aattatattg ggactttgct tgttatcact agttctatcc | 720 |
| atgattttga tggtgataat caggtatata tcaagagtac ttgtgtggat cttaacgatt | 780 |
| ctggtcatac tcggttcact tggaggcaca ggtgtactat ggtggctgta tgcaaagcaa | 840 |
| agaaggtctc ccaaagaaac tgttactcct gagcagcttc agatagctga agacaatctt | 900 |
| cgggccctcc tcatttatgc catttcagct acagtgttca cagtgatctt attcctgata | 960 |
| atgttggtta tgcgcaaacg tgttgctctt accatcgcct tgttccacgt agctggcaag | 1020 |
| gtcttcattc acttgccact gctagtcttc caaccttct ggactttctt tgctcttgtc | 1080 |
| ttgtttggg tgtactggat catgacactt cttttcttg gcactaccgg cagtcctgtt | 1140 |
| cagaatgagc aaggctttgt ggagttcaaa atttctgggc tctgcagta catgtggtgg | 1200 |
| taccatgtgg tgggcctgat ttggatcagt gaatttattc tagcatgtca gcagatgaca | 1260 |
| gtggcaggag ctgtggtaac atactatttt actagggata aaggaatttg ccatttaca | 1320 |
| cctattttgg catcagtaaa tcgccttatt cgttaccacc taggtacggt ggcaaaagga | 1380 |
| tctttcatta tcacattagt caaaattccg cgaatgatcc ttatgtatat tcacagtcag | 1440 |
| ctcaaaggaa aggaaaatgc ttgtgcacga tgtgtgctga atcttgcat ttgttgcctt | 1500 |
| tggtgtcttg aaaagtgcct aaattattta aatcagaatg catacacagc cacagctatc | 1560 |
| aacagcacca acttctgcac ctcagcaaag gatgcctttg tcattctggt ggagaatgct | 1620 |
| ttgcgagtgg ctaccatcaa cacagtagga gattttatgt tattccttgg caaggtgctg | 1680 |
| atagtctgca gcacaggttt agctgggatt atgctgctca actaccagca ggactacaca | 1740 |
| gtatgggtgc tgcctctgat catcgtctgc ctctttgctt tcctagtcgc tcattgcttc | 1800 |
| ctgtctattt atgaaatggt agtggatgta ttattcttgt gttttgccat tgatacaaaa | 1860 |
| tacaatgatg ggagccctgg cagagaattc tatatggata aagtgctgat ggagtttgtg | 1920 |
| gaaaacagta ggaaagcaat gaaagaagct ggtaagggag gcgtcgctga ttccagagag | 1980 |
| ctaaagccga tgctgaagaa aaggtgactg gtctcatgag ccctgaagaa tgaactcaga | 2040 |
| ggaggttgtt tacatgaggt tctcccactc accagctgtt gagagtctgc gattatgaag | 2100 |
| agcaggatct tattacttca atgaaagcat gtaacaagtt tctcaaacca ccaacagcca | 2160 |
| agtggatttg gtacagtgcg gctgtctaat aaataatcaa aagcatttga tagaaaaaaa | 2220 |
| aaaa | 2224 |

<210> SEQ ID NO 2
<211> LENGTH: 2808
<212> TYPE: DNA
<213> ORGANISM: Homo sapiens
<220> FEATURE:
<221> NAME/KEY: modified_base
<222> LOCATION: (1553)
<223> OTHER INFORMATION: a, t, c, g, other or unknown
<220> FEATURE:
<221> NAME/KEY: modified_base
<222> LOCATION: (2682)
<223> OTHER INFORMATION: a, t, c, g, other or unknown
<220> FEATURE:
<221> NAME/KEY: modified_base
<222> LOCATION: (2702)
<223> OTHER INFORMATION: a, t, c, g, other or unknown
<220> FEATURE:
<221> NAME/KEY: modified_base
<222> LOCATION: (2705)
<223> OTHER INFORMATION: a, t, c, g, other or unknown

```
<220> FEATURE:
<221> NAME/KEY: modified_base
<222> LOCATION: (2743)
<223> OTHER INFORMATION: a, t, c, g, other or unknown
<220> FEATURE:
<221> NAME/KEY: modified_base
<222> LOCATION: (2781)
<223> OTHER INFORMATION: a, t, c, g, other or unknown

<400> SEQUENCE: 2
gcggccgccg gggctggtcg cctgcaggga tgggggacga gcggcccac  tactacggga      60 aacacggaac gccacagaag tatgatccca ctttcaaagg acccatttac aataggggct     120
gcacggatat catatgctgt gtgttcctgc tcctggccat tgtgggctac gtggctgtag     180
gcatcatagc ctggactcat ggagaccctc gaaaggtgat ctaccccact gatagccggg     240
gcgagttctg cgggcagaag ggcacaaaaa acgagaacaa accctatctg ttttatttca     300
acattgtgaa atgtgccagc cccctggttc tgctggaatt ccaatgtccc actccccaga     360
tctgcgtgga aaaatgcccc gaccgctacc tcacgtacct gaatgctcgc agctcccggg     420
actttgagta ctataagcag ttctgtgttc ctggcttcaa gaacaataaa ggagtggctg     480
aggtgcttcg agatggtgac tgccctgctg tcctcatccc cagcaaaccc ttggcccgga     540
gatgcttccc cgctatccac gcctacaagg gtgtcctgat ggtgggcaat gagacgacct     600
atgaggatgg gcatggctcc cggaaaaaca tcacagacct ggtggagggc gccaagaaag     660
ccaatggagt cctagaggcg cggcaactcg ccatgcgcat atttgaagat acaccgtctc     720
cttggtactg gattatcata ggcctggtca ttgccatggc gatgagcctc ctgttcatca     780
tcctgcttcg cttcctggct ggtattatgg tctgggtgat gatcatcatg gtgattctgg     840
tgctgggcta cggaatattt cactgctaca tggagtactc ccgactgcgt ggtgaggccg     900
gctctgatgt ctctttggtg gacctcggct ttcagacgga tttccgggtg tacctgcact     960
tacggcagac ctggttggcc tttatgatca ttctgagtat ccttgaagtc attatcatct    1020
tgctgctcat ctttctccgg aagagaattc tcatcgcgat tgcactcatc aaagaagcca    1080
gcagggctgt gggatacgtc atgtgctcct tgctctaccc actggtcacc ttcttcttgc    1140
tgtgcctctg catcgcctac tgggccagca ctgctgtctt cctgtccact ccaacgaag     1200 cggtctataa gatctttgat gacagcccct gcccatttac tgcgaaaacc tgcaacccag    1260
agaccttccc ctcctccaat gagtcccgcc aatgccccaa tgcccgttgc cagttcgcct    1320
tctacggtgg tgagtcgggc taccaccggg ccctgctggg cctgcagatc ttcaatgcct    1380
tcatgttctt ctggttggcc aacttcgtgc tggcgctggg ccaggtcacg ctggccgggg    1440
cctttgcctc ctattactgg gccctgcgca agcggacga cctgccggcc ttcccgctct    1500
tctctgcctt tggccgggcg ctcaggtacc acacaggctc cctggccttt ggngcgctca    1560
tcctggccat tgtgcagatc atccgtgtga tactcgagta cctggatcag cggctgaaag    1620
gtgcagagaa caagtttgcc aagtgcctca tgacctgtct caaatgctgc ttctggtgcc    1680
tggagaagtt catcaaattc cttaatagga atgcctacat catgattgcc atctacggca    1740
ccaatttctg cacctcggcc aggaatgcct tcttcctgct catgagaaac atcatcagag    1800
tggctgtcct ggataaagtt actgacttcc tcttcctgtt gggcaaactt ctgatcgttg    1860
gtagtgtggg gatcctggct ttcttcttct tcacccaccg tatcaggatc gtgcaggata    1920
cagcaccacc cctcaattat tactgggttc ctatactgac ggtgatcgtt ggctcctact    1980
tgattgcaca cggtttcttc agcgtctatg gcatgtgtgt ggacacgctg ttcctctgct    2040
```

-continued

```
tcttggagga cctggagagg aatgacggct cggccgagag gccttacttc atgtcttcca    2100
ccctcaagaa actcttgaac aagaccaaca agaaggcagc ggagtcctga aggcccgtg     2160 ctccccacct ctcaaggagt ctcatgccgc agggtgctca gtagctgggt ctgttccccc    2220 agcccttgg gttcacctga agtcctatca ctgccgctct gccctcccc atgagccaga     2280 tcccaccagt ttctggacgt ggagagtctg gggcatctcc ttcttatgcc aagggggcgct   2340 tggagttttc atggctgccc ctccagactg cgagaaacaa gtaaaaaccc wttggggcct   2400
cttgatgtct gggatggcac gtggcccgac ctccacaagc tccctcatgc ttcctgtccc    2460
ccgcttacac gacaacgggc cagaccacag gaaggacggt gtttgtgtct gagggagctg   2520
ctggccacag tgaacaccca cgtttattcc tgcctgctcc ggccaggact gaacccttc    2580 tccacacctg aacagttggc tcaagggcca ccagaagcat ttctttatta ttattatttt   2640
ttaacctgga catgcattaa agggtctatt agctttcttt yncgtctgtc tcaacagctg   2700 anatngggc cgccaaggag tgcctttcct tttgcttcct tcntaggttg gagttaacgg    2760
gtgggaagtt tttttttccca ngtgggggtg ttttcctggt tgggaagg               2808
```

<210> SEQ ID NO 3
<211> LENGTH: 654
<212> TYPE: PRT
<213> ORGANISM: Homo sapiens

<400> SEQUENCE: 3

```
Met Gly Cys Cys Ser Ser Ala Ser Ser Ala Ala Gln Ser Ser Lys Arg
 1               5                   10                  15

Glu Trp Lys Pro Leu Glu Asp Arg Ser Cys Thr Asp Ile Pro Trp Leu
                20                  25                  30

Leu Leu Phe Ile Leu Phe Cys Ile Gly Met Gly Phe Ile Cys Gly Phe
            35                  40                  45

Ser Ile Ala Thr Gly Ala Ala Ala Arg Leu Val Ser Gly Tyr Asp Ser
        50                  55                  60

Tyr Gly Asn Ile Arg Gly Gln Lys Asn Thr Lys Leu Glu Ala Ile Pro
65                  70                  75                  80

Asn Ser Gly Met Asp His Thr Gln Arg Lys Tyr Val Phe Phe Leu Asp
                85                  90                  95

Pro Cys Asn Leu Asp Leu Ile Asn Arg Lys Ile Lys Ser Val Ala Leu
            100                 105                 110

Cys Val Ala Ala Cys Pro Arg Gln Glu Leu Lys Thr Leu Ser Asp Val
        115                 120                 125

Gln Lys Phe Ala Glu Ile Asn Gly Ser Ala Leu Cys Ser Tyr Asn Leu
    130                 135                 140

Lys Pro Ser Glu Tyr Thr Thr Ser Pro Lys Ser Ser Val Leu Cys Pro
145                 150                 155                 160

Lys Leu Pro Val Pro Ala Ser Ala Pro Ile Pro Phe Phe His Arg Cys
                165                 170                 175

Ala Pro Val Asn Ile Ser Cys Tyr Ala Lys Phe Ala Glu Ala Leu Ile
            180                 185                 190

Thr Phe Val Ser Asp Asn Ser Val Leu His Arg Leu Ile Ser Gly Val
        195                 200                 205

Met Thr Ser Lys Glu Ile Ile Leu Gly Leu Cys Leu Leu Ser Leu Val
    210                 215                 220

Leu Ser Met Ile Leu Met Val Ile Ile Arg Tyr Ile Ser Arg Val Leu
225                 230                 235                 240
```

-continued

```
Val Trp Ile Leu Thr Ile Leu Val Ile Leu Gly Ser Leu Gly Gly Thr
            245                 250                 255
Gly Val Leu Trp Trp Leu Tyr Ala Lys Gln Arg Arg Ser Pro Lys Glu
        260                 265                 270
Thr Val Thr Pro Glu Gln Leu Gln Ile Ala Glu Asp Asn Leu Arg Ala
    275                 280                 285
Leu Leu Ile Tyr Ala Ile Ser Ala Thr Val Phe Thr Val Ile Leu Phe
290                 295                 300
Leu Ile Met Leu Val Met Arg Lys Arg Val Ala Leu Thr Ile Ala Leu
305                 310                 315                 320
Phe His Val Ala Gly Lys Val Phe Ile His Leu Pro Leu Leu Val Phe
                325                 330                 335
Gln Pro Phe Trp Thr Phe Phe Ala Leu Val Leu Phe Trp Val Tyr Trp
            340                 345                 350
Ile Met Thr Leu Leu Phe Leu Gly Thr Thr Gly Ser Pro Val Gln Asn
        355                 360                 365
Glu Gln Gly Phe Val Glu Phe Lys Ile Ser Gly Pro Leu Gln Tyr Met
    370                 375                 380
Trp Trp Tyr His Val Val Gly Leu Ile Trp Ile Ser Glu Phe Ile Leu
385                 390                 395                 400
Ala Cys Gln Gln Met Thr Val Ala Gly Ala Val Val Thr Tyr Tyr Phe
                405                 410                 415
Thr Arg Asp Lys Arg Asn Leu Pro Phe Thr Pro Ile Leu Ala Ser Val
            420                 425                 430
Asn Arg Leu Ile Arg Tyr His Leu Gly Thr Val Ala Lys Gly Ser Phe
        435                 440                 445
Ile Ile Thr Leu Val Lys Ile Pro Arg Met Ile Leu Met Tyr Ile His
    450                 455                 460
Ser Gln Leu Lys Gly Lys Glu Asn Ala Cys Ala Arg Cys Val Leu Lys
465                 470                 475                 480
Ser Cys Ile Cys Cys Leu Trp Cys Leu Glu Lys Cys Leu Asn Tyr Leu
                485                 490                 495
Asn Gln Asn Ala Tyr Thr Ala Thr Ala Ile Asn Ser Thr Asn Phe Cys
            500                 505                 510
Thr Ser Ala Lys Asp Ala Phe Val Ile Leu Val Glu Asn Ala Leu Arg
        515                 520                 525
Val Ala Thr Ile Asn Thr Val Gly Asp Phe Met Leu Phe Leu Gly Lys
    530                 535                 540
Val Leu Ile Val Cys Ser Thr Gly Leu Ala Gly Ile Met Leu Leu Asn
545                 550                 555                 560
Tyr Gln Gln Asp Tyr Thr Val Trp Val Leu Pro Leu Ile Ile Val Cys
                565                 570                 575
Leu Phe Ala Phe Leu Val Ala His Cys Phe Leu Ser Ile Tyr Glu Met
            580                 585                 590
Val Val Asp Val Leu Phe Leu Cys Phe Ala Ile Asp Thr Lys Tyr Asn
        595                 600                 605
Asp Gly Ser Pro Gly Arg Glu Phe Tyr Met Asp Lys Val Leu Met Glu
    610                 615                 620
Phe Val Glu Asn Ser Arg Lys Ala Met Lys Glu Ala Gly Lys Gly Gly
625                 630                 635                 640
Val Ala Asp Ser Arg Glu Leu Lys Pro Met Leu Lys Lys Arg
                645                 650
```

-continued

```
<210> SEQ ID NO 4
<211> LENGTH: 706
<212> TYPE: PRT
<213> ORGANISM: Homo sapiens

<400> SEQUENCE: 4
```

| | | | | | | | | | | | | | | |
|---|---|---|---|---|---|---|---|---|---|---|---|---|---|---|
| Met | Gly | Asp | Glu | Arg | Pro | His | Tyr | Tyr | Gly | Lys | His | Gly | Thr | Pro | Gln |
| 1 | | | | 5 | | | | | 10 | | | | | 15 |

| Lys | Tyr | Asp | Pro | Thr | Phe | Lys | Gly | Pro | Ile | Tyr | Asn | Arg | Gly | Cys | Thr |
|---|---|---|---|---|---|---|---|---|---|---|---|---|---|---|---|
| | | | 20 | | | | | 25 | | | | | 30 | | |

| Asp | Ile | Ile | Cys | Cys | Val | Phe | Leu | Leu | Leu | Ala | Ile | Val | Gly | Tyr | Val |
|---|---|---|---|---|---|---|---|---|---|---|---|---|---|---|---|
| | | | 35 | | | | | 40 | | | | | 45 | | |

| Ala | Val | Gly | Ile | Ile | Ala | Trp | Thr | His | Gly | Asp | Pro | Arg | Lys | Val | Ile |
|---|---|---|---|---|---|---|---|---|---|---|---|---|---|---|---|
| | 50 | | | | | 55 | | | | | 60 | | | | |

| Tyr | Pro | Thr | Asp | Ser | Arg | Gly | Glu | Phe | Cys | Gly | Gln | Lys | Gly | Thr | Lys |
|---|---|---|---|---|---|---|---|---|---|---|---|---|---|---|---|
| 65 | | | | | 70 | | | | | 75 | | | | | 80 |

| Asn | Glu | Asn | Lys | Pro | Tyr | Leu | Phe | Tyr | Phe | Asn | Ile | Val | Lys | Cys | Ala |
|---|---|---|---|---|---|---|---|---|---|---|---|---|---|---|---|
| | | | | 85 | | | | | 90 | | | | | 95 | |

| Ser | Pro | Leu | Val | Leu | Leu | Glu | Phe | Gln | Cys | Pro | Thr | Pro | Gln | Ile | Cys |
|---|---|---|---|---|---|---|---|---|---|---|---|---|---|---|---|
| | | | | 100 | | | | | 105 | | | | | 110 | |

| Val | Glu | Lys | Cys | Pro | Asp | Arg | Tyr | Leu | Thr | Tyr | Leu | Asn | Ala | Arg | Ser |
|---|---|---|---|---|---|---|---|---|---|---|---|---|---|---|---|
| | | 115 | | | | | 120 | | | | | 125 | | | |

| Ser | Arg | Asp | Phe | Glu | Tyr | Tyr | Lys | Gln | Phe | Cys | Val | Pro | Gly | Phe | Lys |
|---|---|---|---|---|---|---|---|---|---|---|---|---|---|---|---|
| | 130 | | | | | 135 | | | | | 140 | | | | |

| Asn | Asn | Lys | Gly | Val | Ala | Glu | Val | Leu | Arg | Asp | Gly | Asp | Cys | Pro | Ala |
|---|---|---|---|---|---|---|---|---|---|---|---|---|---|---|---|
| 145 | | | | | 150 | | | | | 155 | | | | | 160 |

| Val | Leu | Ile | Pro | Ser | Lys | Pro | Leu | Ala | Arg | Arg | Cys | Phe | Pro | Ala | Ile |
|---|---|---|---|---|---|---|---|---|---|---|---|---|---|---|---|
| | | | | 165 | | | | | 170 | | | | | 175 | |

| His | Ala | Tyr | Lys | Gly | Val | Leu | Met | Val | Gly | Asn | Glu | Thr | Thr | Tyr | Glu |
|---|---|---|---|---|---|---|---|---|---|---|---|---|---|---|---|
| | | | 180 | | | | | 185 | | | | | 190 | | |

| Asp | Gly | His | Gly | Ser | Arg | Lys | Asn | Ile | Thr | Asp | Leu | Val | Glu | Gly | Ala |
|---|---|---|---|---|---|---|---|---|---|---|---|---|---|---|---|
| | | 195 | | | | | 200 | | | | | 205 | | | |

| Lys | Lys | Ala | Asn | Gly | Val | Leu | Glu | Ala | Arg | Gln | Leu | Ala | Met | Arg | Ile |
|---|---|---|---|---|---|---|---|---|---|---|---|---|---|---|---|
| | 210 | | | | | 215 | | | | | 220 | | | | |

| Phe | Glu | Asp | Tyr | Thr | Val | Ser | Trp | Tyr | Trp | Ile | Ile | Ile | Gly | Leu | Val |
|---|---|---|---|---|---|---|---|---|---|---|---|---|---|---|---|
| 225 | | | | | 230 | | | | | 235 | | | | | 240 |

| Ile | Ala | Met | Ala | Met | Ser | Leu | Leu | Phe | Ile | Ile | Leu | Leu | Arg | Phe | Leu |
|---|---|---|---|---|---|---|---|---|---|---|---|---|---|---|---|
| | | | | 245 | | | | | 250 | | | | | 255 | |

| Ala | Gly | Ile | Met | Val | Trp | Val | Met | Ile | Ile | Met | Val | Ile | Leu | Val | Leu |
|---|---|---|---|---|---|---|---|---|---|---|---|---|---|---|---|
| | | | 260 | | | | | 265 | | | | | 270 | | |

| Gly | Tyr | Gly | Ile | Phe | His | Cys | Tyr | Met | Glu | Tyr | Ser | Arg | Leu | Arg | Gly |
|---|---|---|---|---|---|---|---|---|---|---|---|---|---|---|---|
| | | 275 | | | | | 280 | | | | | 285 | | | |

| Glu | Ala | Gly | Ser | Asp | Val | Ser | Leu | Val | Asp | Leu | Gly | Phe | Gln | Thr | Asp |
|---|---|---|---|---|---|---|---|---|---|---|---|---|---|---|---|
| | 290 | | | | | 295 | | | | | 300 | | | | |

| Phe | Arg | Val | Tyr | Leu | His | Leu | Arg | Gln | Thr | Trp | Leu | Ala | Phe | Met | Ile |
|---|---|---|---|---|---|---|---|---|---|---|---|---|---|---|---|
| 305 | | | | | 310 | | | | | 315 | | | | | 320 |

| Ile | Leu | Ser | Ile | Leu | Glu | Val | Ile | Ile | Leu | Leu | Ile | Phe | Leu |
|---|---|---|---|---|---|---|---|---|---|---|---|---|---|
| | | | | 325 | | | | | 330 | | | | | 335 |

| Arg | Lys | Arg | Ile | Leu | Ile | Ala | Ile | Ala | Leu | Ile | Lys | Glu | Ala | Ser | Arg |
|---|---|---|---|---|---|---|---|---|---|---|---|---|---|---|---|
| | | | 340 | | | | | 345 | | | | | 350 | | |

| Ala | Val | Gly | Tyr | Val | Met | Cys | Ser | Leu | Leu | Tyr | Pro | Leu | Val | Thr | Phe |
|---|---|---|---|---|---|---|---|---|---|---|---|---|---|---|---|
| | | 355 | | | | | 360 | | | | | 365 | | | |

| Phe | Leu | Leu | Cys | Leu | Cys | Ile | Ala | Tyr | Trp | Ala | Ser | Thr | Ala | Val | Phe |
|---|---|---|---|---|---|---|---|---|---|---|---|---|---|---|---|
| | 370 | | | | | 375 | | | | | 380 | | | | |

-continued

```
Leu Ser Thr Ser Asn Glu Ala Val Tyr Lys Ile Phe Asp Asp Ser Pro
385                 390                 395                 400

Cys Pro Phe Thr Ala Lys Thr Cys Asn Pro Glu Thr Phe Pro Ser Ser
            405                 410                 415

Asn Glu Ser Arg Gln Cys Pro Asn Ala Arg Cys Gln Phe Ala Phe Tyr
        420                 425                 430

Gly Gly Glu Ser Gly Tyr His Arg Ala Leu Leu Gly Leu Gln Ile Phe
    435                 440                 445

Asn Ala Phe Met Phe Phe Trp Leu Ala Asn Phe Val Leu Ala Leu Gly
    450                 455                 460

Gln Val Thr Leu Ala Gly Ala Phe Ala Ser Tyr Tyr Trp Ala Leu Arg
465                 470                 475                 480

Lys Pro Asp Asp Leu Pro Ala Phe Pro Leu Phe Ser Ala Phe Gly Arg
            485                 490                 495

Ala Leu Arg Tyr His Thr Gly Ser Leu Ala Phe Val Ala Leu Ile Leu
        500                 505                 510

Ala Ile Val Gln Ile Ile Arg Val Ile Leu Glu Tyr Leu Asp Gln Arg
        515                 520                 525

Leu Lys Gly Ala Glu Asn Lys Phe Ala Lys Cys Leu Met Thr Cys Leu
530                 535                 540

Lys Cys Cys Phe Trp Cys Leu Glu Lys Phe Ile Lys Phe Leu Asn Arg
545                 550                 555                 560

Asn Ala Tyr Ile Met Ile Ala Ile Tyr Gly Thr Asn Phe Cys Thr Ser
                565                 570                 575

Ala Arg Asn Ala Phe Phe Leu Leu Met Arg Asn Ile Ile Arg Val Ala
        580                 585                 590

Val Leu Asp Lys Val Thr Asp Phe Leu Phe Leu Leu Gly Lys Leu Leu
        595                 600                 605

Ile Val Gly Ser Val Gly Ile Leu Ala Phe Phe Phe Thr His Arg
    610                 615                 620

Ile Arg Ile Val Gln Asp Thr Ala Pro Pro Leu Asn Tyr Tyr Trp Val
625                 630                 635                 640

Pro Ile Leu Thr Val Ile Val Gly Ser Tyr Leu Ile Ala His Gly Phe
                645                 650                 655

Phe Ser Val Tyr Gly Met Cys Val Asp Thr Leu Phe Leu Cys Phe Leu
                660                 665                 670

Glu Asp Leu Glu Arg Asn Asp Gly Ser Ala Glu Arg Pro Tyr Phe Met
        675                 680                 685

Ser Ser Thr Leu Lys Lys Leu Leu Asn Lys Thr Asn Lys Lys Ala Ala
    690                 695                 700

Glu Ser
705
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
caaaattggc tagagaaaca accg         24

<210> SEQ ID NO 6
<211> LENGTH: 23
<212> TYPE: DNA

-continued

<213> ORGANISM: Artificial Sequence
<220> FEATURE:
<223> OTHER INFORMATION: Description of Artificial Sequence: Primer

<400> SEQUENCE: 6
aaagaacaat ggccttatac agg                                    23

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
catgtggtgg taccatgtgg tggg                                   24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
cgaataaggc gatttactga tgcc                                   24

<210> SEQ ID NO 9
<211> LENGTH: 657
<212> TYPE: PRT
<213> ORGANISM: Homo sapiens

<400> SEQUENCE: 9

Met Gly Cys Cys Ser Ser Ala Ser Ser Ala Ala Gln Ser Ser Lys Arg
 1               5                  10                  15

Glu Trp Lys Pro Leu Glu Asp Arg Ser Cys Thr Asp Ile Pro Trp Leu
                20                  25                  30

Leu Leu Phe Ile Leu Phe Cys Ile Gly Met Gly Phe Ile Cys Gly Phe
            35                  40                  45

Ser Ile Ala Thr Gly Ala Ala Ala Arg Leu Val Ser Gly Tyr Asp Ser
        50                  55                  60

Tyr Gly Asn Ile Arg Gly Gln Lys Asn Thr Lys Leu Glu Ala Ile Pro
65                  70                  75                  80

Asn Ser Gly Met Asp His Thr Gln Arg Lys Tyr Val Phe Phe Leu Asp
                85                  90                  95

Pro Cys Asn Leu Asp Leu Ile Asn Arg Lys Ile Lys Ser Val Ala Leu
               100                 105                 110

Cys Val Ala Ala Cys Pro Arg Gln Glu Leu Lys Thr Leu Ser Asp Val
           115                 120                 125

Gln Lys Phe Ala Glu Ile Asn Gly Ser Ala Leu Cys Ser Tyr Asn Leu
       130                 135                 140

Lys Pro Ser Glu Tyr Thr Thr Ser Pro Lys Ser Ser Val Leu Cys Pro
145                 150                 155                 160

Lys Leu Pro Val Pro Ala Ser Ala Pro Ile Pro Phe His Arg Cys
               165                 170                 175

Ala Pro Val Asn Ile Ser Cys Tyr Ala Lys Phe Ala Glu Ala Leu Ile
           180                 185                 190

Thr Phe Val Ser Asp Asn Ser Val Leu His Arg Leu Ile Ser Gly Val
       195                 200                 205

```
Met Thr Ser Lys Glu Ile Ile Leu Gly Leu Cys Leu Leu Ser Leu Val
210                 215                 220

Leu Ser Met Ile Leu Met Val Ile Ile Arg Tyr Ile Ser Arg Val Leu
225                 230                 235                 240

Val Trp Ile Leu Thr Ile Leu Val Ile Leu Gly Ser Leu Gly Gly Thr
                245                 250                 255

Gly Val Leu Trp Trp Leu Tyr Ala Lys Gln Arg Arg Ser Pro Lys Glu
            260                 265                 270

Thr Val Thr Pro Glu Gln Leu Gln Ile Ala Glu Asp Asn Leu Arg Ala
        275                 280                 285

Leu Leu Ile Tyr Ala Ile Ser Ala Thr Val Phe Thr Val Ile Leu Phe
    290                 295                 300

Leu Ile Met Leu Val Met Arg Lys Arg Val Ala Leu Thr Ile Ala Leu
305                 310                 315                 320

Phe His Val Ala Gly Lys Val Phe Ile His Leu Pro Leu Leu Val Phe
                325                 330                 335

Gln Pro Phe Trp Thr Phe Phe Ala Leu Val Leu Phe Trp Val Tyr Trp
            340                 345                 350

Ile Met Thr Leu Leu Phe Leu Gly Thr Thr Gly Ser Pro Val Gln Asn
        355                 360                 365

Glu Gln Gly Phe Val Glu Phe Lys Ile Ser Gly Pro Leu Gln Tyr Met
    370                 375                 380

Trp Trp Tyr His Val Val Gly Leu Ile Trp Ile Ser Glu Phe Ile Leu
385                 390                 395                 400

Ala Cys Gln Gln Met Thr Val Ala Gly Ala Val Val Thr Tyr Tyr Phe
                405                 410                 415

Thr Arg Asp Lys Arg Asn Leu Pro Phe Thr Pro Ile Leu Ala Ser Val
            420                 425                 430

Asn Arg Leu Ile Arg Tyr His Leu Gly Thr Val Ala Lys Gly Ser Phe
        435                 440                 445

Ile Ile Thr Leu Val Lys Ile Pro Arg Met Ile Leu Met Tyr Ile His
    450                 455                 460

Ser Gln Leu Lys Gly Lys Glu Asn Ala Cys Ala Arg Cys Val Leu Lys
465                 470                 475                 480

Ser Cys Ile Cys Cys Leu Trp Cys Leu Glu Lys Cys Leu Asn Tyr Leu
                485                 490                 495

Asn Gln Asn Ala Tyr Thr Ala Thr Ala Ile Asn Ser Thr Asn Phe Cys
            500                 505                 510

Thr Ser Ala Lys Asp Ala Phe Val Ile Leu Val Glu Asn Ala Leu Arg
        515                 520                 525

Val Ala Thr Ile Asn Thr Val Gly Asp Phe Met Leu Phe Leu Gly Lys
    530                 535                 540

Val Leu Ile Val Cys Ser Thr Gly Leu Ala Gly Ile Met Leu Leu Asn
545                 550                 555                 560

Tyr Gln Gln Asp Tyr Thr Val Trp Val Leu Pro Leu Ile Ile Val Cys
                565                 570                 575

Leu Phe Ala Phe Leu Val Ala His Cys Phe Leu Ser Ile Tyr Glu Met
            580                 585                 590

Val Val Asp Val Leu Phe Leu Cys Phe Ala Ile Asp Thr Lys Tyr Asn
        595                 600                 605

Asp Gly Ser Pro Gly Arg Glu Phe Tyr Met Asp Lys Val Leu Met Glu
    610                 615                 620

Phe Val Glu Asn Ser Arg Lys Ala Met Lys Glu Ala Gly Lys Gly Gly
```

-continued

```
                625                 630                 635                 640
Val Ala Asp Ser Arg Glu Leu Lys Pro Met Ala Ser Gly Ala Ser Ser
                    645                 650                 655
Ala

<210> SEQ ID NO 10
<211> LENGTH: 646
<212> TYPE: PRT
<213> ORGANISM: Torpedo marmorata

<400> SEQUENCE: 10

Met Gly Cys Cys Gly Cys Gly Ser Glu Glu Gly Ser Val Arg Gln Trp
 1               5                  10                  15

Lys Pro Leu Glu Gln Arg Ser Cys Thr Asp Val Leu Trp Leu Leu Ile
             20                  25                  30

Phe Val Leu Phe Cys Ile Gly Met Ala Ile Ile Cys Gly Phe Ala Ile
         35                  40                  45

Ala Ser Gly Ala Ala Gln Arg Leu Val Phe Gly Tyr Asp Ser Tyr Gly
     50                  55                  60

Asn Ile Cys Gly His Lys Asn Thr Glu Ile Lys Asp Val Thr Met Ser
 65                  70                  75                  80

Gly Leu Asp His Thr Asp Lys Lys Tyr Val Phe Phe Glu Pro Cys
                 85                  90                  95

Asn Trp Asp Met Val His Leu Lys Ile Leu Ser Val Ala Leu Cys Val
            100                 105                 110

Thr Lys Cys Pro Asp Met Asp Leu Lys Thr Leu Glu Asp Val Arg Asn
        115                 120                 125

Phe Ala Lys Tyr Asn Gly Ser Arg Leu Cys Leu Tyr Asn Leu Asp Pro
    130                 135                 140

Thr Gln Tyr Thr Ser Lys Asn Ser Lys Ser Cys Pro Ile Leu Pro Val
145                 150                 155                 160

Lys Ser Ser Lys Pro Ile Pro Phe Phe His Arg Cys Val Pro Met Asp
                165                 170                 175

Ser Gly Cys Lys Ile Asn Phe Lys Ala Leu Thr Thr Phe Val Ser Tyr
            180                 185                 190

Asn Ser Val Leu Gln Arg Val Ile Thr Gly Val Met Thr Ser Lys Glu
        195                 200                 205

Ile Ile Val Gly Leu Cys Leu Met Ser Leu Val Leu Ser Ile Leu Leu
    210                 215                 220

Met Val Ile Ile Arg Tyr Ile Ser Lys Val Leu Val Trp Ile Leu Ala
225                 230                 235                 240

Ile Leu Thr Ile Ile Gly Ser Ile Gly Gly Thr Ala Val Leu Trp Trp
                245                 250                 255

Leu Tyr Ala Asp His Lys Lys Thr Leu Lys Leu Asp Pro Ser Gln Gly
            260                 265                 270

Asp Val Ala Ala Asp Asn Val Thr Ala Leu Leu Val Cys Ala Ile Ile
        275                 280                 285

Ala Thr Val Ile Thr Val Ile Leu Leu Leu Leu Met Leu Ile Met Arg
    290                 295                 300

Lys Arg Val Ala Leu Thr Ile Ala Leu Phe His Val Ala Gly Lys Val
305                 310                 315                 320

Phe Ile His Ile Pro Phe Leu Ile Phe Gln Ser Leu Trp Thr Phe Leu
                325                 330                 335

Ala Leu Ala Phe Phe Trp Ile Tyr Trp Ile Ala Val Leu Leu Leu Leu
```

-continued

```
                    340                 345                 350
Ala Thr Ala Gly Tyr Pro Gln Lys Lys Asp Gln Gly Tyr Val Glu Phe
                355                 360                 365
Lys Val Ser Gly Pro Leu Gln Tyr Thr Trp Ile Tyr His Leu Val Gly
            370                 375                 380
Leu Ile Trp Ile Ser Glu Phe Ile Leu Ala Cys Gln Gln Met Thr Ile
385                 390                 395                 400
Ala Gly Ala Val Val Thr Tyr Tyr Phe Thr Arg Asp Lys His Asn Leu
                405                 410                 415
Pro Ala Thr Pro Ile Leu Ala Ser Met Cys Arg Leu Ile Lys Tyr His
                420                 425                 430
Leu Gly Thr Val Ala Lys Gly Ser Phe Ile Ile Thr Leu Ile Lys Ile
            435                 440                 445
Pro Gln Met Ile Leu Val Tyr Ile His Ser Gln Leu Lys Gly Lys Glu
            450                 455                 460
Asn Ala Cys Ala Lys Cys Met Leu Lys Ala Cys Met Cys Cys Leu Trp
465                 470                 475                 480
Cys Leu Glu Lys Cys Leu Leu Tyr Leu Asn Arg Asn Ala Tyr Ile Ala
                485                 490                 495
Thr Ser Ile Asn Val Thr Ser Phe Cys Thr Ser Ala Lys Asp Ala Ile
                500                 505                 510
Val Ile Leu Val Glu Asn Ala Met Arg Val Ala Ala Ile Asn Thr Val
            515                 520                 525
Gly Asp Phe Val Leu Phe Leu Gly Lys Leu Leu Ile Val Leu Val Thr
            530                 535                 540
Gly Phe Val Gly Ile Ile Leu Leu Asn Tyr Gln Arg Asp Tyr Thr Val
545                 550                 555                 560
Trp Val Leu Pro Leu Ile Ile Cys Leu Phe Ala Phe Phe Val Ser
                565                 570                 575
His Cys Phe Leu Ser Ile Tyr Glu Met Val Val Asp Val Leu Phe Leu
                580                 585                 590
Cys Phe Ala Val Asp Cys Lys His Asn Asp Gly Ser Pro Gly Arg Glu
            595                 600                 605
Tyr Tyr Met Asp Lys Ser Leu Met Glu Phe Met Asp Glu Ser Arg Lys
            610                 615                 620
Ala Met Arg Ser Val Thr Gly Ser Gly Ala Glu Met Lys Ser Met Ala
625                 630                 635                 640
Ser Gly Ser Asp Asn Ala
                645

<210> SEQ ID NO 11
<211> LENGTH: 653
<212> TYPE: PRT
<213> ORGANISM: Rattus sp.

<400> SEQUENCE: 11

Met Gly Cys Cys Ser Ser Ala Ser Ala Ala Gln Ser Ser Lys Arg Glu
1               5                   10                  15
Trp Lys Pro Leu Glu Asp Arg Ser Cys Thr Asp Ile Pro Trp Leu Leu
                20                  25                  30
Leu Phe Val Leu Phe Cys Ile Gly Met Gly Phe Ile Cys Gly Phe Ser
            35                  40                  45
Val Ala Thr Gly Ala Ala Ala Arg Leu Val Ser Gly Tyr Asp Ser Tyr
        50                  55                  60
```

-continued

```
Gly Asn Ile Cys Gly Gln Arg Asn Ala Lys Leu Glu Ala Ile Ala Asn
 65                  70                  75                  80

Ser Gly Leu Asp His Thr His Arg Lys Tyr Val Phe Leu Asp Pro
             85                  90                  95

Cys Asn Leu Asp Leu Ile Asn Arg Lys Ile Lys Ser Met Ala Leu Cys
             100                 105                 110

Val Ala Ala Cys Pro Arg Gln Glu Leu Lys Thr Leu Ser Asp Val Gln
         115                 120                 125

Lys Phe Ala Glu Ile Asn Gly Ser Ala Leu Cys Ser Tyr Asn Ile Lys
130                 135                 140

Pro Ser Glu Tyr Thr Leu Thr Ala Lys Ser Ser Ala Phe Cys Pro Lys
145                 150                 155                 160

Leu Pro Val Pro Ala Ser Ala Pro Ile Pro Phe Phe His Arg Cys Ala
                 165                 170                 175

Pro Val Asn Ile Ser Cys Tyr Ala Lys Phe Ala Glu Ala Leu Ile Thr
             180                 185                 190

Phe Val Ser Asp Asn Ser Val Leu His Arg Leu Ile Ser Gly Val Met
         195                 200                 205

Thr Ser Lys Glu Ile Ile Leu Gly Leu Cys Leu Leu Ser Leu Val Leu
210                 215                 220

Ser Met Ile Leu Met Val Ile Ile Arg Tyr Ile Ser Arg Val Leu Val
225                 230                 235                 240

Trp Ile Leu Thr Ile Leu Val Ile Leu Gly Ser Leu Gly Gly Thr Gly
                 245                 250                 255

Val Leu Trp Trp Leu Tyr Ala Lys Gln Arg Ser Ser Pro Lys Glu Thr
             260                 265                 270

Val Ile Pro Glu Gln Leu Gln Ile Ala Glu Asp Asn Leu Arg Ala Leu
         275                 280                 285

Leu Ile Tyr Ala Ile Ser Ala Thr Val Phe Thr Val Ile Leu Phe Leu
290                 295                 300

Ile Met Leu Val Met Arg Lys Arg Val Ala Leu Thr Ile Ala Leu Phe
305                 310                 315                 320

His Val Ala Gly Lys Val Phe Ile His Leu Pro Leu Leu Val Phe Gln
                 325                 330                 335

Pro Phe Trp Thr Phe Ala Leu Val Leu Phe Trp Ala Tyr Trp Ile
             340                 345                 350

Met Thr Leu Leu Phe Leu Gly Thr Thr Gly Ser Ala Val Gln Asn Glu
             355                 360                 365

Gln Gly Phe Val Glu Tyr Lys Ile Ser Gly Pro Leu Gln Tyr Met Trp
370                 375                 380

Trp Tyr His Val Val Gly Leu Ile Trp Ile Ser Glu Phe Ile Leu Ala
385                 390                 395                 400

Cys Gln Gln Met Thr Val Ala Gly Ala Val Val Thr Tyr Tyr Phe Thr
             405                 410                 415

Arg Asp Lys Arg Asn Leu Pro Phe Thr Pro Ile Leu Ala Ser Val Asn
         420                 425                 430

Arg Leu Ile Arg Tyr His Leu Gly Thr Val Ala Lys Gly Ser Phe Ile
             435                 440                 445

Ile Thr Leu Val Lys Ile Pro Arg Met Ile Leu Met Tyr Ile His Ser
         450                 455                 460

Gln Leu Lys Gly Lys Glu Asn Ala Cys Ala Arg Cys Met Leu Lys Ser
465                 470                 475                 480

Cys Ile Cys Cys Leu Trp Cys Leu Glu Lys Cys Leu Ser Tyr Leu Asn
```

-continued

```
                485                 490                 495
Gln Asn Ala Tyr Thr Ala Thr Ala Ile Asn Ser Thr Asn Phe Cys Thr
            500                 505                 510

Ser Ala Lys Asp Ala Phe Val Ile Leu Val Glu Asn Ala Leu Arg Val
        515                 520                 525

Ala Ala Ile Asn Thr Val Gly Asp Phe Met Leu Phe Leu Gly Lys Val
    530                 535                 540

Leu Ile Val Cys Ser Thr Gly Leu Ala Gly Ile Met Leu Leu Asn Tyr
545                 550                 555                 560

Gln Gln Asp Tyr Thr Val Trp Val Leu Pro Leu Ile Ile Val Cys Leu
                565                 570                 575

Phe Ala Phe Leu Val Ala His Cys Phe Leu Ser Ile Tyr Glu Met Val
            580                 585                 590

Val Asp Val Leu Phe Leu Cys Phe Ala Ile Asp Thr Lys Tyr Asn Asp
        595                 600                 605

Gly Ser Pro Gly Arg Glu Phe Tyr Met Asp Lys Val Leu Met Glu Phe
    610                 615                 620

Val Glu Asn Ser Arg Lys Ala Met Lys Glu Ala Gly Lys Gly Gly Ala
625                 630                 635                 640

Ala Asp Ala Arg Glu Leu Lys Pro Met Leu Arg Lys Arg
                645                 650

<210> SEQ ID NO 12
<211> LENGTH: 712
<212> TYPE: PRT
<213> ORGANISM: Homo sapiens

<400> SEQUENCE: 12

Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Ile Thr Pro Pro Ala Leu
            180                 185                 190

Pro Gly Ile Thr Asn Asp Thr Thr Ile Gln Gln Gly Ile Ser Gly Leu
        195                 200                 205
```

-continued

```
Ile Asp Ser Leu Asn Ala Arg Asp Ile Ser Val Lys Ile Phe Glu Asp
    210                 215                 220
Phe Ala Gln Ser Trp Tyr Trp Ile Leu Val Ala Leu Gly Val Ala Leu
225                 230                 235                 240
Val Leu Ser Leu Leu Phe Ile Leu Leu Arg Leu Val Ala Gly Pro
                    245                 250                 255
Leu Val Leu Val Leu Ile Leu Gly Val Leu Gly Val Leu Ala Tyr Gly
                260                 265                 270
Ile Tyr Tyr Cys Trp Glu Glu Tyr Arg Val Leu Arg Asp Lys Gly Ala
        275                 280                 285
Ser Ile Ser Gln Leu Gly Phe Thr Thr Asn Leu Ser Ala Tyr Gln Ser
    290                 295                 300
Val Gln Glu Thr Trp Leu Ala Ala Leu Ile Val Leu Ala Val Leu Glu
305                 310                 315                 320
Ala Ile Leu Leu Leu Val Leu Ile Phe Leu Arg Gln Arg Ile Arg Ile
                325                 330                 335
Ala Ile Ala Leu Leu Lys Glu Ala Ser Lys Ala Val Gly Gln Met Met
                340                 345                 350
Ser Thr Met Phe Tyr Pro Leu Val Thr Phe Val Leu Leu Ile Cys
                355                 360                 365
Ile Ala Tyr Trp Ala Met Thr Ala Leu Tyr Pro Leu Pro Thr Gln Pro
370                 375                 380
Ala Thr Leu Gly Tyr Val Leu Trp Ala Ser Asn Ile Ser Ser Pro Gly
385                 390                 395                 400
Cys Glu Lys Val Pro Ile Asn Thr Ser Cys Asn Pro Thr Ala His Leu
                405                 410                 415
Val Asn Ser Ser Cys Pro Gly Leu Met Cys Val Phe Gln Gly Tyr Ser
                420                 425                 430
Ser Lys Gly Leu Ile Gln Arg Ser Val Phe Asn Leu Gln Ile Tyr Gly
            435                 440                 445
Val Leu Gly Leu Phe Trp Thr Leu Asn Trp Val Leu Ala Leu Gly Gln
    450                 455                 460
Cys Val Leu Ala Gly Ala Phe Ala Ser Phe Tyr Trp Ala Phe His Lys
465                 470                 475                 480
Pro Gln Asp Ile Pro Thr Phe Pro Leu Ile Ser Ala Phe Ile Arg Thr
                485                 490                 495
Leu Arg Tyr His Thr Gly Ser Leu Ala Phe Gly Ala Leu Ile Leu Thr
                500                 505                 510
Leu Val Gln Ile Ala Arg Val Ile Leu Glu Tyr Ile Asp His Lys Leu
            515                 520                 525
Arg Gly Val Gln Asn Pro Val Ala Arg Cys Ile Met Cys Cys Phe Lys
    530                 535                 540
Cys Cys Leu Trp Cys Leu Glu Lys Phe Ile Lys Phe Leu Asn Arg Asn
545                 550                 555                 560
Ala Tyr Ile Met Ile Ala Ile Tyr Gly Lys Asn Phe Cys Val Ser Ala
                565                 570                 575
Lys Asn Ala Phe Met Leu Leu Met Arg Asn Ile Val Arg Val Val Val
                580                 585                 590
Leu Asp Lys Val Thr Asp Leu Leu Phe Gly Lys Leu Leu Val
            595                 600                 605
Val Gly Gly Val Gly Val Leu Ser Phe Phe Phe Ser Gly Arg Ile
    610                 615                 620
Pro Gly Leu Gly Lys Asp Phe Lys Ser Pro His Leu Asn Tyr Tyr Trp
```

```
                625                 630                 635                 640
Leu Pro Ile Met Thr Ser Ile Leu Gly Ala Tyr Val Ile Ala Ser Gly
                    645                 650                 655

Phe Phe Ser Val Phe Gly Met Cys Val Asp Thr Leu Phe Leu Cys Phe
                660                 665                 670

Leu Glu Asp Leu Glu Arg Asn Asn Gly Ser Leu Asp Arg Pro Tyr Tyr
                675                 680                 685

Met Ser Lys Ser Leu Leu Lys Ile Leu Gly Lys Lys Asn Glu Ala Pro
            690                 695                 700

Pro Asp Asn Lys Lys Arg Lys Lys
705                 710

<210> SEQ ID NO 13
<211> LENGTH: 771
<212> TYPE: PRT
<213> ORGANISM: Caenorhabditis elegans

<400> SEQUENCE: 13

Met Gly Arg Lys Lys His Arg Thr Ile Pro Ala Val Glu Val Tyr Glu
  1               5                  10                  15

Lys Ser Asp Gly Phe Pro Met Pro Thr Ala Pro Pro Met Ser Pro Ser
                 20                  25                  30

Arg Met Asp Gly Val Tyr Pro Ser His Val Pro Pro Leu His Gln
             35                  40                  45

Ala Tyr His Val Gln Pro Ala Ser Ala Asn His Val Pro Asp Gln Ile
         50                  55                  60

Ala Arg Phe Asn Val Ile Lys Pro Asp Arg Leu Ala Lys Arg His Asn
 65                  70                  75                  80

Pro Gln Leu Tyr Thr Lys Arg Gly Cys Thr Asp Val Phe Cys Cys Phe
                 85                  90                  95

Leu Phe Val Phe Leu Cys Gly Trp Val Val Ala Gly Phe Gly
                100                 105                 110

Ile Met Trp Gly Asp Pro Gln Arg Leu Ile Tyr Pro Thr Asp Ser Glu
            115                 120                 125

Phe Arg Arg Cys Gly Val Asn Leu Glu Gly Ser Tyr Asn Phe Ser Lys
130                 135                 140

Arg Pro Tyr Leu Phe Tyr Phe Asp Leu Thr Lys Cys Ile Ser Tyr Ala
145                 150                 155                 160

Thr Ala Leu Gly Gly Cys Gln Thr Thr Gln Leu Cys Val Lys Glu Cys
                165                 170                 175

Pro Ser Thr Tyr Phe Ser Tyr Leu Gln Leu Arg Thr Ala Ser Val Ser
                180                 185                 190

Glu Ile Gln Asn Lys Met Lys Ser Val Val Tyr Cys Thr Asp Asp Val
            195                 200                 205

Asp Lys Thr Thr Val Thr Thr Phe Gln Ala Leu Gln Asn Leu Val Gln
210                 215                 220

Arg Gly Lys Cys Val Ser Tyr Thr Val Lys Ser Val Pro Val Leu Gln
225                 230                 235                 240

Arg Cys Phe Pro Glu Ala Ile Phe Asn Ala Val Asp Asn Val Asn Asn
                245                 250                 255

Val Leu Asn Ser Ser Asn Ser Leu Asp Tyr Leu Lys Arg Thr Phe Gly
                260                 265                 270

Asp Asp Ala Leu Ile Pro Gln Asp Ile Gln Ile Thr Gly Gln Ser Ser
            275                 280                 285
```

-continued

```
Glu Val Met Lys Ser Val Val Glu Asp Gln Pro Val Thr His Lys Val
290                 295                 300
Ile His Asp Leu Ser Gln Thr Trp Trp Gln Thr Leu Ile Leu Ile Phe
305                 310                 315                 320
Ala Ala Gly Ile Leu Ser Phe Ile Trp Thr Val Ile Met Arg Leu Leu
                325                 330                 335
Gly Ser Leu Ile Ile Trp Leu Ser Ile Leu Ile Val Leu Val Ala Leu
                340                 345                 350
Gly Phe Gly Ala Gly Phe Ser Trp Leu Lys Trp Asn Thr Leu Lys Thr
            355                 360                 365
Thr Gly Ala Ile Asp Asp Tyr Ser Phe His Pro Ala Phe Asp Ala Tyr
370                 375                 380
Phe Glu Met Pro Thr Thr Trp Leu Val Val Ala Ile Ala Thr Ser Val
385                 390                 395                 400
Leu Leu Leu Ile Phe Leu Leu Val Ile Leu Phe Ile Arg Gln Arg Ile
                405                 410                 415
Ser Ile Ala Cys Ala Leu Ile Ser Glu Ser Ser Lys Ala Ile Gly Ser
                420                 425                 430
Met Met Ser Thr Leu Leu Phe Pro Leu Phe Pro Phe Leu Leu His Ile
            435                 440                 445
Gly Val Phe Ala Leu Trp Gly Ser Ile Ala Ile Trp Leu Ala Ser Ser
450                 455                 460
Gly Gln Glu Val Cys Arg Leu Lys Glu Thr Asn Gly Gln Val Tyr Asn
465                 470                 475                 480
Thr Ser Thr Lys Cys Asp Cys Thr Ala Lys Val Thr Gly Cys Thr Tyr
                485                 490                 495
Val Gly Ile Glu Lys Glu Ser Glu Thr Ile Phe Trp Leu Gln Val Tyr
                500                 505                 510
Asn Leu Phe Ala Phe Phe Trp Leu Ser Cys Phe Val Thr Ala Leu Gly
            515                 520                 525
Asp Ile Ala Leu Ala Gly Ala Phe Ala Ser Tyr Tyr Trp Ala Arg Asp
530                 535                 540
Lys Arg His Asp Val Pro Thr Phe Pro Val Ile Arg Ala Leu Asn Arg
545                 550                 555                 560
Ala Ile Arg Tyr Asn Leu Gly Ser Ile Ala Phe Gly Ser Leu Ile Ile
                565                 570                 575
Ala Ile Val Lys Ile Ile Arg Val Leu Leu Glu Tyr Ile Asp His Lys
                580                 585                 590
Leu Gly Lys Ser Gln Asn Lys Ala Val Lys Trp Phe Leu Met Cys Leu
            595                 600                 605
Lys Cys Cys Phe Trp Cys Leu Glu Val Phe Phe Lys Phe Leu Thr Lys
610                 615                 620
Asn Ala Tyr Ile Met Ile Ala Ile Tyr Gly Lys Asn Phe Phe Ser Ser
625                 630                 635                 640
Ala Lys Asp Ser Phe Leu Leu Ile Thr Arg Asn Ile Val Arg Thr Val
                645                 650                 655
Val Val His Lys Val Ala Gly Ile Leu Leu Phe Leu Gly Lys Ser Met
                660                 665                 670
Ile Thr Leu Gly Met Gly Ile Leu Ser Phe Tyr Tyr Phe Ser Gly Arg
            675                 680                 685
Trp Val Val Glu Gly Val Pro Lys Val Asp Leu Tyr Tyr Tyr Phe Val
690                 695                 700
Pro Ile Val Ile Val Val Ile Gly Ser Tyr Phe Met Ala Asp Leu Phe
```

```
                705                 710                 715                 720
Phe Asp Val Tyr Glu Met Ala Val Asp Thr Thr Phe Ile Cys Phe Leu
                    725                 730                 735

Glu Asp Ser Glu Gln Asn Asp Gly Ser Leu Glu Arg Pro Phe Phe Met
                740                 745                 750

Ser Glu Lys Leu Leu Glu Ile Leu Gly Asn Lys Asn Asp Ile Pro Leu
            755                 760                 765

His Ser Lys
    770

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide used in naming yeast strain

<400> SEQUENCE: 14

Leu His His His His
  1               5
```